(12) United States Patent
Bergstrand et al.

(10) Patent No.: US 6,228,373 B1
(45) Date of Patent: May 8, 2001

(54) PEPTIDES WITH IMMUNOMODULATORY EFFECTS

(75) Inventors: Håkan Bergstrand, Bjärred; Tomas Eriksson, Lund; Magnus Lindvall, Lund; Bengt Särnstrand, Lund, all of (SE)

(73) Assignee: Astra Aktiebolag (SE)

( * ) Notice: Subject to any disclaimer, the term of this patent is extended or adjusted under 35 U.S.C. 154(b) by 0 days.

(21) Appl. No.: 08/750,142

(22) PCT Filed: Mar. 22, 1996

(86) PCT No.: PCT/SE96/00365

§ 371 Date: Nov. 25, 1996

§ 102(e) Date: Nov. 25, 1996

(87) PCT Pub. No.: WO96/30397

PCT Pub. Date: Oct. 3, 1996

(30) Foreign Application Priority Data

Mar. 24, 1995 (SE) .................................................. 9501067

(51) Int. Cl.[7] .............................. A61K 45/05; C07K 7/00
(52) U.S. Cl. .............................. 424/278.1; 514/2; 514/17; 514/62; 530/300
(58) Field of Search .................................. 530/326, 327, 530/328, 329, 330, 333, 300; 424/185.1, 278.1; 514/2, 12–18, 62

(56) References Cited

U.S. PATENT DOCUMENTS

| | | | |
|---|---|---|---|
| 4,585,755 | 4/1986 | Morgan et al. | 514/11 |
| 4,822,606 | 4/1989 | Snyderman et al. | 424/88 |
| 5,223,485 | 6/1993 | Kawai et al. | 514/16 |
| 5,780,508 | * 7/1998 | Andersson et al. | 514/562 |

FOREIGN PATENT DOCUMENTS

| | | |
|---|---|---|
| 0 341 603 | 5/1989 | (EP) . |
| WO 88/05783 | 8/1988 | (WO) . |
| WO 9204445 | 3/1992 | (WO) . |
| WO 93/00108 | 1/1993 | (WO) . |
| WO 9308279 | 4/1993 | (WO) . |
| WO 94/20127 | 9/1994 | (WO) . |
| WO 95/01182 | 1/1995 | (WO) . |
| WO 95/20599 | 8/1995 | (WO) . |
| WO 96/01318 | 1/1996 | (WO) . |
| WO 96/11943 | 4/1996 | (WO) . |

OTHER PUBLICATIONS

Karin et al., Reversal of experimental autoimmune encephalomyelitis by a soluble peptide variant of a myelin basic protein epitope, J. Exp. Med., 180:2227–2237 (Dec. 1994).*
Wilding et al., Targeting of drugs and vaccines to the gut, Pharmac. Ther., 62: 97–124 (1994).*
Stites et al., Eds., Basic and Clinical Immunology, 8th ed., Appleton & Lange:Norwalk, CT, pp. 572–574, 712–714, 762, 1994.*
Andreu et al., "Formation of Disulfide Bonds in Synthetic Peptides and Proteins", Methods in Molecular Biology, vol. 35, (1994).
Arnone et al., "The DNA Binding Activity and the Dimerization Ability of the Thyroid Transcription . . . ", J. Biological Chemistry, vol. 270, No. 20, 12048–12055, (1995).
Balcewicz–Sablinska et al., "Human Eosinophil Cytotoxicity–Enhancing Factor, II. Multiple Forms Synthesized by U937 Cells . . . ", J. of Immunology 147, 2170–2174 (Oct. 1, 1991).
Bannister et al., "In vitro DNA binding activity of Fos/Jun and BZLF1 but not C/EBP is affected by redox changes", Oncogene 6, 1243–1250 (1991).
Beckmann et al., "Preparation of chemically "mutated" aprotinin homologues by semisynthesis . . . ", FEBS 1988—EJB 88 0141.
Bergstrand et al., "Stimuli–induced Superoxide Radical Generation In Vitro by Human Alveolar Macrophages from Smokers . . . ", J. of Free Radicals in Biol. & Medicine, vol. 2, 119–127, (1986).
Bushweller et al., "Structural and Functional Characterization of the Mutant *Escherichia coli* Glutaredoxin . . . ", Biochemistry, 31, 9288–9293; (1992).
Louis A. Carpino, "1–Hydroxy–7–azabenzotriazole. An Efficient Peptide Coupling Additive", J. Am. Chem. Soc., 115, 4397–4398 (1993).
Chalmers et al., Pro–D–NMe–Amino Acid and D–Pro–N–Me–Amino Acid. Simple, Efficient Reverse–Turn Constraints J. Amer. Chem. Soc., 117, 5927–5937; (1995).
Chen et al., "Costimulation of T cells for tumor immunity", Immunology Today, 483, vol. 14, No. 10, (1993).
Civitareale et al., "Purification and characterization of thyroid transcription factor2", Biochem. J.,304, 981–985 (1994).
Clarke et al., "Identification of molecules involved in the "early pregnancy factor" phenomenon", J. Reprod. Fert. 93, 525–539, (1991).
Deiss et al., "A Genetic Tool Used to Identify Thioredoxin as a Mediator of a Growth Inhibitory Signal" Science, vol. 252, 117–120 (Apr. 1991).
Verhoef et al., "Clonal analysis of the atopic immune response to the group 2 allergen of Dermatophagoides spp.: identification . . . ", International Immunology, vol. 5, No. 12, 1589–1597 (1993).
Droge et al., "Functions of glutathione and glutathione disulfide in immunology and immunopathology", Reviews, FASEB Journal vol. 8, 0892–6638/0008–1131, (1994).
Dryland et al, "Peptide Synthesis, Part 8, A System for Solid–phase Synthesis Under Low Pressure Continuous Flow Conditions", J. Chem. Soc. Perkin Trans. 1 (1986).

(List continued on next page.)

Primary Examiner—Claire M. Kaufman
(74) Attorney, Agent, or Firm—Fish & Richardson P.C.

(57) ABSTRACT

Peptides being absorbable by the epithelial cell lining in a mammal resulting in a modulated immune response and thereby a therapeutic effect against disease, formulations containing such peptides and uses thereof.

92 Claims, No Drawings

OTHER PUBLICATIONS

Espinoza–Delgado et al., "Regulation of IL–2 Receptor Subunit Genes in Human Monocytes; Differential Effects of . . . ", Journal of Immunology, vol. 149, No. 9, 2961–2968, No. 9 (1992).

Esposito et al., "DNA binding activity of the glucocorticoid receptor is sensitive to redox changes in intact cells", Biochimica et Biophysica Acta 1260, 308–314; (1995).

Flegel et al., "A Sensitive, General Method for Quantitative Monitoring of Continuous Flow Solid Phase Peptide Synthesis", J. Chem. Soc., Chem. Commun., 536–538; (1990).

Grasso et al., "A synthetic peptide corresponding to hFSH–β–(81–95) has thioredoxin–like activity", Molecular and Cellular Endocrinology, 78 163–170 (1991).

Grippo et al., "Proof that the Endogenous, Heat–stable Glucocorticoid Receptor–activating Factor Is Thioredoxin", The Journal of Biological Chemistry, vol. 260, No. 1, 93–97, (1985).

Hansson et al., "T lymphocytes inhibit the vascular response to injury", Proc. Natl. Acad. Sci. USA, vol. 88, 10530–10534, (1991).

Arne Holmgren, "Thioredoxin and Glutaredoxin Systems" The Journal of Biol. Chemistry, vol. 264, No. 24, 13963–13966, (1989).

Huang et al., "Characterization of the DNA–Binding Properties of the Early Growth Response–1 (Egr–1) Transcription . . . " DNA and Cell Biology, vol. 12, No. 3, 265–273, (1993).

John Jones, "The Chemical Synthesis of Peptides" Balliol College, Oxford (1991).

Kasafirek et al., "Amino Acids and Peptides, LXVI Synthesis of Ten Extended–chain Analogues of Lysine Vasopressin", Collection Czechoslov. Chem. Commun. vol. 31, (1966).

David H. Katz, "The Allergic Phenotype: Manifestation of "Allergic Breakthrough" and Imbalance in Normal "Damping" of IgE Antibody Production", Immunological Rev., vol. 41 (1978).

Khananshvili et al., "Positively Charged Cyclic Hexapeptides, Novel Blockers for the Cardiac Sarcolemma . . . " The Journal of Biological Chemistry, vol. 270, No. 27, 16182–16188, (1995).

Knoepfel et al., "role of Zinc–Coordination and of the Glutathione Redox Couple in the Redox Susceptibility of Human Transcription Factor SP1", Biochem. and Biophysical Res. Comm. vol. 201, No. 2, (1994).

McBride et al., "Conserved cysteine residue in the DNA–binding domain of the bovine papillomavirus type 1 E2 protein confers redox regulation of the DNA–binding activity in vitro", Proc. Natl. Acad. Sci, 89,(1992).

Cornelis J. M. Melief, "Tumor Eradication by Adoptive Transfer of Cytotoxic T Lymphocytes", Advances in Cancer Research ; 58:143–75 (1992).

Miele et al., "Novel anti–inflammatory peptides from the region of highest similarity between uteroglobin and lipocortin I", Nature, vol. 335,726–730 (1988).

Mitomo et al., "Two different cellular redox systems regulate the DNA–binding activity of the p50 subunit of NF–κB in vitro", Gene, 145, 197–203,(1994).

Nicolas et al., "A Study of the Use of NH4I for the Reduction of Methionine Sulfoxide in Peptides containing Cysteine . . . ", Tetrahedron, vol. 51, No. 19, 5701–5710, (1995).

Noiva et al., "Protein Disulfide Isomerase; A Multifunctional Protein Resident in the Lumen of the Endoplasmic Reticulum", J. of Biological Chemistry, vol. 267, No. 6, 3553–3556, (1992).

Patel et al., "Sulfhydryl–Disulfide Modulation and the Role of Disulfide Oxidoreductases in Regulation of the Catalytic Activity . . . ", Am. J. Respir. Cell Mol. Biol., vol. 13, 352–359, (1995).

Paul, "Representative Autoimmune Diseases and thier Animal Models", Fundamental Immunology, 2nd Ed., 31:840–866, (1989).

Paupe, "Immunotherapy with an Oral Bacterial Extract (OM–85BV) for Upper Respiratory Infections", Respiration, 58:150–154, (1991).

Pohl et al., "Cyclic disulfide analogues of the complement component C3a", Int. J. Peptide Protein Res. 41, 362–375 (1993).

Radermecker et al., "Increase in the Number and the Phagocytic Function of Guinea Pig Pulmonary and Peritoneal Macrophages . . . ", Int. J. Immunopharmac., vol. 10, No. 8, 913–917 (1988).

Rosenberg, "Immunotherapy of cancer using interleukin 2:" Immunology Today, vol. 9, No. 2, 58–62 (1988).

Roszman et al., "Modulation of T–cell function by gliomas", Immunology Today, vol. 12, No. 10, 370–374 (1991).

Ruiz–Gayo et al., "Uteroglobin–like Peptide Cavities I. Synthesis of Antiparrallel and Parallel Dimers of Bis–Cysteine Peptides", Tetrahedron Letters, vol. 29, No. 31, 3845–3848 (1988).

Salerno et al., "Covalent Modification with Concomitant Inactivation of the cAMP–dependent Protein Kinase by Affinity Labels . . . ", The Journal of Biological Chemistry, vol. 266, No. 18, 13043–13049 (1993).

Scheffer et al., "Effect of an Immunostimulatory Substance of *Klebsiella pneumoniae* on Inflammatory Responses . . .", Arzneim.–Forsch./Drug Res. 41 (II), 815–820 (1991).

Schulze–Osthoff et al., "Redox Signalling by Transcription Factors NF–κB and AP–1 in Lymphocytes" Biochemical Pharmacology, vol. 50, No. 6 735–741 (1995).

Sheppard et al., "Acid–labile resin linkage agents for use in solid phase peptide synthesis", Int. J. Peptide Protein Res., 20, 455–467 (1982).

Shimotohno et al., "Identification of new gene products coded from X regions of human T–cell leukemia viruses", Proc. Natl. Acad. Sci. USA vol. 82, 302–306 (1985).

Singh et al., "Application of Genetic Algorithms to Combinatorial Synthesis: A Computational Approach to Lead Identification and Lead Optimization", J. Am. Chem. Soc., 118, 1669–1676, (1996).

Spinella et al., "Endothelin–receptor interactions of a putative sulfhydryl on the endothelin receptor" FEBS Letters, vol. 328, 82–88 (1993).

Spinella et al., "Design and synthesis of a specific endothelin 1 antagonist: Effects on pulmonary vasoconstriction", Proc. Natl. Acad. Sci. USA, vol. 88, 7443–7446, (1991).

Stevenson, "Tumor vaccines", The FASEB Journal, vol. 5, 2250–2257 (1991).

Van Wauwe et al., "Review Article on the biochemical Mode of Action of Levamisole: An Update", Int. J. Immunopharmac., vol. 13, No. 1, 3–9 (1991).

Varela et al., "Second generation immune networks", Immunology Today, vol. 12, No. 5, 159–166 (1991).

von Geldern et al., "Small Atrial Natriuretic Peptide Analogues: Design, Synthesis, and Structural Requirements for Guanylate Cyclase Activation", J. Med. Chem. 35, 808–816 (1992).

Xanthoudakis et al., "The redox and DNA–repair activities of Ref–1 are encoded by nonoverlapping domains" Proc. Natl. Acad. Sci. USA, vol. 91, 23–27 (1994).

Xanthoudakis et al., "Analysis of c–Fos and c–Jun Redox–Dependent DNA Binding Activity", Methods in Enzymology, vol. 234, 163–174 (1994).

Yao et al., "Activation of AP–1 and of a Nuclear Redox Factor, Ref–1, in the Response of HT29 Colon Cancer Cells to Hypoxia", Molecular and Cellular Biology, vol., 14, No. 9, 5997–6003 (1994).

Yodoi et al., "Diseases associated with HTLV–I: virus, IL–2 receptor dysregulation and redox regulation", Immunology Today, vol. 13, No. 10, 405–411 (1992).

Zhang et al., "Suppression of diabetes in nonobese diabetic mice by oral administration of porcine insulin", Proc. Natl. Acad. Sci USA, vol. 88, 10252–10256 (1991).

International Search Report; International Application No. PCT/SE 95/01151; (Oct. 6, 1995).

International Search Report; International Application No. SE 95/00312; (Mar. 24, 1995).

International Search Report; PCT/JP95/00082; (May 2, 1995).

* cited by examiner

SEQUENCE LISTING (1) GENERAL INFORMATION:

(iii) NUMBER OF SEQUENCES: 55

(2) INFORMATION FOR SEQ ID NO: 1:

(i) SEQUENCE CHARACTERISTICS:
      (A) LENGTH: 4 amino acids
      (B) TYPE: amino acid
      (D) TOPOLOGY: linear (ii) MOLECULE TYPE: peptide (xi) SEQUENCE DESCRIPTION: SEQ ID NO: 1:

```
Xaa Cys Cys Tyr
  1
```

(2) INFORMATION FOR SEQ ID NO: 2:

(i) SEQUENCE CHARACTERISTICS:
        (A) LENGTH: 4 amino acids
        (B) TYPE: amino acid
        (D) TOPOLOGY: linear (ii) MOLECULE TYPE: peptide (xi) SEQUENCE DESCRIPTION: SEQ ID NO: 2:

```
Gly Cys Cys Gly
  1
```

(2) INFORMATION FOR SEQ ID NO: 3:

(i) SEQUENCE CHARACTERISTICS:
        (A) LENGTH: 4 amino acids
        (B) TYPE: amino acid
        (D) TOPOLOGY: linear (ii) MOLECULE TYPE: peptide (xi) SEQUENCE DESCRIPTION: SEQ ID NO: 3:

```
Pro Cys Cys Pro
  1
```

(2) INFORMATION FOR SEQ ID NO: 4:

(i) SEQUENCE CHARACTERISTICS:
        (A) LENGTH: 4 amino acids
        (B) TYPE: amino acid
        (D) TOPOLOGY: linear (ii) MOLECULE TYPE: peptide (xi) SEQUENCE DESCRIPTION: SEQ ID NO: 4:

```
Pro Cys Cys Val
  1
```

(2) INFORMATION FOR SEQ ID NO: 5:

(i) SEQUENCE CHARACTERISTICS:
        (A) LENGTH: 4 amino acids
        (B) TYPE: amino acid
        (D) TOPOLOGY: linear (ii) MOLECULE TYPE: peptide (xi) SEQUENCE DESCRIPTION: SEQ ID NO: 5:

```
Ile Cys Cys Leu
  1
```

(2) INFORMATION FOR SEQ ID NO: 6:

(i) SEQUENCE CHARACTERISTICS:
        (A) LENGTH: 4 amino acids
        (B) TYPE: amino acid
        (D) TOPOLOGY: linear (ii) MOLECULE TYPE: peptide (xi) SEQUENCE DESCRIPTION: SEQ ID NO: 6:

```
Pro Cys Cys Glu
  1
```

(2) INFORMATION FOR SEQ ID NO: 7:

(i) SEQUENCE CHARACTERISTICS:
        (A) LENGTH: 4 amino acids
        (B) TYPE: amino acid
        (D) TOPOLOGY: linear (ii) MOLECULE TYPE: peptide (xi) SEQUENCE DESCRIPTION: SEQ ID NO: 7:

Glu Cys Cys Tyr
1

(2) INFORMATION FOR SEQ ID NO: 8:

(i) SEQUENCE CHARACTERISTICS:
        (A) LENGTH: 4 amino acids
        (B) TYPE: amino acid
        (D) TOPOLOGY: linear (ii) MOLECULE TYPE: peptide (xi) SEQUENCE DESCRIPTION: SEQ ID NO: 8:

Pro Cys Cys Phe
1

(2) INFORMATION FOR SEQ ID NO: 9:

(i) SEQUENCE CHARACTERISTICS:
        (A) LENGTH: 4 amino acids
        (B) TYPE: amino acid
        (D) TOPOLOGY: linear (ii) MOLECULE TYPE: peptide (xi) SEQUENCE DESCRIPTION: SEQ ID NO: 9:

Glu Cys Cys Phe
1

(2) INFORMATION FOR SEQ ID NO: 10:

(i) SEQUENCE CHARACTERISTICS:
        (A) LENGTH: 4 amino acids
        (B) TYPE: amino acid
        (D) TOPOLOGY: linear (ii) MOLECULE TYPE: peptide (xi) SEQUENCE DESCRIPTION: SEQ ID NO: 10:

Ala Cys Cys Val
1

(2) INFORMATION FOR SEQ ID NO: 11:

(i) SEQUENCE CHARACTERISTICS:
        (A) LENGTH: 4 amino acids
        (B) TYPE: amino acid
        (D) TOPOLOGY: linear (ii) MOLECULE TYPE: peptide (xi) SEQUENCE DESCRIPTION: SEQ ID NO: 11:

Val Cys Cys Ile
1

(2) INFORMATION FOR SEQ ID NO: 12:

(i) SEQUENCE CHARACTERISTICS:
        (A) LENGTH: 4 amino acids

-continued (B) TYPE: amino acid
        (D) TOPOLOGY: linear (ii) MOLECULE TYPE: peptide (xi) SEQUENCE DESCRIPTION: SEQ ID NO: 12:

Gln Cys Cys Ser
1

(2) INFORMATION FOR SEQ ID NO: 13:

(i) SEQUENCE CHARACTERISTICS:
        (A) LENGTH: 4 amino acids
        (B) TYPE: amino acid
        (D) TOPOLOGY: linear (ii) MOLECULE TYPE: peptide (xi) SEQUENCE DESCRIPTION: SEQ ID NO: 13:

Ile Cys Cys Thr
1

(2) INFORMATION FOR SEQ ID NO: 14:

(i) SEQUENCE CHARACTERISTICS:
        (A) LENGTH: 4 amino acids
        (B) TYPE: amino acid
        (D) TOPOLOGY: linear (ii) MOLECULE TYPE: peptide (xi) SEQUENCE DESCRIPTION: SEQ ID NO: 14:

Leu Cys Cys Asp
1

(2) INFORMATION FOR SEQ ID NO: 15:

(i) SEQUENCE CHARACTERISTICS:
        (A) LENGTH: 4 amino acids
        (B) TYPE: amino acid
        (D) TOPOLOGY: linear (ii) MOLECULE TYPE: peptide (xi) SEQUENCE DESCRIPTION: SEQ ID NO: 15:

Asp Cys Cys Ile
1

(2) INFORMATION FOR SEQ ID NO: 16:

(i) SEQUENCE CHARACTERISTICS:
        (A) LENGTH: 4 amino acids
        (B) TYPE: amino acid
        (D) TOPOLOGY: linear (ii) MOLECULE TYPE: peptide (xi) SEQUENCE DESCRIPTION: SEQ ID NO: 16:

Leu Cys Cys Gln
1

(2) INFORMATION FOR SEQ ID NO: 17:

(i) SEQUENCE CHARACTERISTICS:
        (A) LENGTH: 4 amino acids
        (B) TYPE: amino acid
        (D) TOPOLOGY: linear (ii) MOLECULE TYPE: peptide

```
            (xi) SEQUENCE DESCRIPTION: SEQ ID NO: 17:

Gly Cys Cys Asn
  1

(2) INFORMATION FOR SEQ ID NO: 18:

(i) SEQUENCE CHARACTERISTICS:
            (A) LENGTH: 4 amino acids
            (B) TYPE: amino acid
            (D) TOPOLOGY: linear (ii) MOLECULE TYPE: peptide (xi) SEQUENCE DESCRIPTION: SEQ ID NO: 18:

Gly Cys Cys Pro
  1

(2) INFORMATION FOR SEQ ID NO: 19:

(i) SEQUENCE CHARACTERISTICS:
            (A) LENGTH: 4 amino acids
            (B) TYPE: amino acid
            (D) TOPOLOGY: linear (ii) MOLECULE TYPE: peptide (xi) SEQUENCE DESCRIPTION: SEQ ID NO: 19:

Ala Cys Cys Gly
  1

(2) INFORMATION FOR SEQ ID NO: 20:

(i) SEQUENCE CHARACTERISTICS:
            (A) LENGTH: 6 amino acids
            (B) TYPE: amino acid
            (D) TOPOLOGY: linear (ii) MOLECULE TYPE: peptide (xi) SEQUENCE DESCRIPTION: SEQ ID NO: 20:

Gly Pro Cys Cys Pro Gly
  1               5

(2) INFORMATION FOR SEQ ID NO: 21:

(i) SEQUENCE CHARACTERISTICS:
            (A) LENGTH: 6 amino acids
            (B) TYPE: amino acid
            (D) TOPOLOGY: linear (ii) MOLECULE TYPE: peptide (xi) SEQUENCE DESCRIPTION: SEQ ID NO: 21:

Ala Pro Cys Cys Val Pro
  1               5

(2) INFORMATION FOR SEQ ID NO: 22:

(i) SEQUENCE CHARACTERISTICS:
            (A) LENGTH: 6 amino acids
            (B) TYPE: amino acid
            (D) TOPOLOGY: linear (ii) MOLECULE TYPE: peptide (xi) SEQUENCE DESCRIPTION: SEQ ID NO: 22:

Lys Pro Cys Cys Glu Arg
```

(2) INFORMATION FOR SEQ ID NO: 23:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (xi) SEQUENCE DESCRIPTION: SEQ ID NO: 23:

Pro Asp Cys Cys Ile Pro
1               5

(2) INFORMATION FOR SEQ ID NO: 24:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (xi) SEQUENCE DESCRIPTION: SEQ ID NO: 24:

Pro Gly Cys Cys Gly Pro
1               5

(2) INFORMATION FOR SEQ ID NO: 25:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (ix) FEATURE:
        (A) NAME/KEY: Disulfide-bond
        (B) LOCATION: 3...4

(xi) SEQUENCE DESCRIPTION: SEQ ID NO: 25:

Trp Pro Cys Cys Pro Trp
1               5

(2) INFORMATION FOR SEQ ID NO: 26:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (ix) FEATURE:
        (A) NAME/KEY: Disulfide-bond
        (B) LOCATION: 3...4

(xi) SEQUENCE DESCRIPTION: SEQ ID NO: 26:

Val Ile Cys Cys Leu Thr
1               5

(2) INFORMATION FOR SEQ ID NO: 27:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (xi) SEQUENCE DESCRIPTION: SEQ ID NO: 27:

Thr Pro Cys Cys Phe Ala
  1               5

(2) INFORMATION FOR SEQ ID NO: 28:

(i) SEQUENCE CHARACTERISTICS:
         (A) LENGTH: 6 amino acids
         (B) TYPE: amino acid
         (D) TOPOLOGY: linear (ii) MOLECULE TYPE: peptide (ix) FEATURE:
         (A) NAME/KEY: Disulfide-bond
         (B) LOCATION: 3...4

(xi) SEQUENCE DESCRIPTION: SEQ ID NO: 28:

Glu Glu Cys Cys Phe Tyr
  1               5

(2) INFORMATION FOR SEQ ID NO: 29:

(i) SEQUENCE CHARACTERISTICS:
         (A) LENGTH: 6 amino acids
         (B) TYPE: amino acid
         (D) TOPOLOGY: linear (ii) MOLECULE TYPE: peptide (ix) FEATURE:
         (A) NAME/KEY: Disulfide-bond
         (B) LOCATION: 3...4

(xi) SEQUENCE DESCRIPTION: SEQ ID NO: 29:

Lys Leu Cys Cys Asp Ile
  1               5

(2) INFORMATION FOR SEQ ID NO: 30:

(i) SEQUENCE CHARACTERISTICS:
         (A) LENGTH: 6 amino acids
         (B) TYPE: amino acid
         (D) TOPOLOGY: linear (ii) MOLECULE TYPE: peptide (xi) SEQUENCE DESCRIPTION: SEQ ID NO: 30:

Lys Glu Cys Cys Tyr Val
  1               5

(2) INFORMATION FOR SEQ ID NO: 31:

(i) SEQUENCE CHARACTERISTICS:
         (A) LENGTH: 7 amino acids
         (B) TYPE: amino acid
         (D) TOPOLOGY: linear (ii) MOLECULE TYPE: peptide (ix) FEATURE:
         (A) NAME/KEY: Other
         (B) LOCATION: 1...1
         (D) OTHER INFORMATION: where Xaa at position 1 is Ala, Cys,
             Asp, Glu, Phe, Gly, His, Ile, Lys, Leu, Met, Asn, Pro,
             Gln, Arg, Ser, Thr, Val, Trp, or Tyr
         (A) NAME/KEY: Other
         (B) LOCATION: 2...2
         (D) OTHER INFORMATION: where Xaa at position 2 is Ala, Asp,
             Glu, Gly, Ile, Leu, Pro, Gln, or Val (A) NAME/KEY: Other
        (B) LOCATION: 7...7
        (D) OTHER INFORMATION: where Xaa at position 7 is Ala, Cys,
            Asp, Glu, Phe, Gly, His, Ile, Lys, Leu, Met, Asn, Pro,
            Gln, Arg, Ser, Thr, Val, Trp, or Tyr (xi) SEQUENCE DESCRIPTION: SEQ ID NO: 31:

Xaa Xaa Cys Glx Cys Tyr Xaa
 1               5

(2) INFORMATION FOR SEQ ID NO: 32:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (xi) SEQUENCE DESCRIPTION: SEQ ID NO: 32:

Lys Leu Cys Cys Gln Met
 1               5

(2) INFORMATION FOR SEQ ID NO: 33:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (xi) SEQUENCE DESCRIPTION: SEQ ID NO: 33:

Pro Gly Cys Xaa Gly Pro
 1               5

(2) INFORMATION FOR SEQ ID NO: 34:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (xi) SEQUENCE DESCRIPTION: SEQ ID NO: 34:

Pro Gly Xaa Cys Gly Pro
 1               5

(2) INFORMATION FOR SEQ ID NO: 35:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (xi) SEQUENCE DESCRIPTION: SEQ ID NO: 35:

Pro Gly Xaa Xaa Gly Pro
 1               5

(2) INFORMATION FOR SEQ ID NO: 36:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (xi) SEQUENCE DESCRIPTION: SEQ ID NO: 36:

Phe Cys Ile Cys Lys
 1               5

(2) INFORMATION FOR SEQ ID NO: 37:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (xi) SEQUENCE DESCRIPTION: SEQ ID NO: 37:

Arg Cys Ser Gly Cys Cys Asn
 1               5

(2) INFORMATION FOR SEQ ID NO: 38:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (ix) FEATURE:
        (A) NAME/KEY: Disulfide-bond
        (B) LOCATION: 3...4

(xi) SEQUENCE DESCRIPTION: SEQ ID NO: 38:

Thr Pro Cys Cys Phe Ala
 1               5

(2) INFORMATION FOR SEQ ID NO: 39:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (xi) SEQUENCE DESCRIPTION: SEQ ID NO: 39:

Ala Val Trp Thr Pro Cys Tyr
 1               5

(2) INFORMATION FOR SEQ ID NO: 40:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (xi) SEQUENCE DESCRIPTION: SEQ ID NO: 40:

Phe Val Met Ala Pro Cys Phe
 1               5

(2) INFORMATION FOR SEQ ID NO: 41:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (xi) SEQUENCE DESCRIPTION: SEQ ID NO: 41:

Leu Leu Tyr Ser Pro Cys Phe
 1               5

(2) INFORMATION FOR SEQ ID NO: 42:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (xi) SEQUENCE DESCRIPTION: SEQ ID NO: 42:

Ile Ser Gly Pro Cys Pro Lys
 1               5

(2) INFORMATION FOR SEQ ID NO: 43:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (xi) SEQUENCE DESCRIPTION: SEQ ID NO: 43:

Phe Leu Phe Gly Pro Cys Ile
 1               5

(2) INFORMATION FOR SEQ ID NO: 44:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (xi) SEQUENCE DESCRIPTION: SEQ ID NO: 44:

Leu Phe Gly Pro Cys Ile Leu
 1               5

(2) INFORMATION FOR SEQ ID NO: 45:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (xi) SEQUENCE DESCRIPTION: SEQ ID NO: 45:

Glu Lys Gly Pro Cys Tyr Arg
 1               5

(2) INFORMATION FOR SEQ ID NO: 46:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (xi) SEQUENCE DESCRIPTION: SEQ ID NO: 46:

```
Phe Cys Leu Gly Pro Cys Pro
  1               5

(2) INFORMATION FOR SEQ ID NO: 47:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (xi) SEQUENCE DESCRIPTION: SEQ ID NO: 47:

Phe Gly Pro Cys Ile
  1               5

(2) INFORMATION FOR SEQ ID NO: 48:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (xi) SEQUENCE DESCRIPTION: SEQ ID NO: 48:

Phe Leu Phe Gly Pro Cys Ile Leu Asn
  1               5

(2) INFORMATION FOR SEQ ID NO: 49:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (xi) SEQUENCE DESCRIPTION: SEQ ID NO: 49:

Gly Pro Cys Ile Leu Asn Arg
  1               5

(2) INFORMATION FOR SEQ ID NO: 50:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (xi) SEQUENCE DESCRIPTION: SEQ ID NO: 50:

Leu Leu Phe Trp Pro Cys Ile
  1               5

(2) INFORMATION FOR SEQ ID NO: 51:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (xi) SEQUENCE DESCRIPTION: SEQ ID NO: 51:

Leu Leu Phe Gly Ile Cys Ile
  1               5
```

(2) INFORMATION FOR SEQ ID NO: 52:

(i) SEQUENCE CHARACTERISTICS:
       (A) LENGTH: 9 amino acids
       (B) TYPE: amino acid
       (D) TOPOLOGY: linear (ii) MOLECULE TYPE: peptide (xi) SEQUENCE DESCRIPTION: SEQ ID NO: 52:

Leu Leu Phe Gly Pro Cys Ile Leu Asn
 1               5

(2) INFORMATION FOR SEQ ID NO: 53:

(i) SEQUENCE CHARACTERISTICS:
       (A) LENGTH: 10 amino acids
       (B) TYPE: amino acid
       (D) TOPOLOGY: linear (ii) MOLECULE TYPE: peptide (xi) SEQUENCE DESCRIPTION: SEQ ID NO: 53:

Leu Leu Phe Gly Pro Cys Ile Leu Asn Arg
 1               5                  10

(2) INFORMATION FOR SEQ ID NO: 54:

(i) SEQUENCE CHARACTERISTICS:
       (A) LENGTH: 12 amino acids
       (B) TYPE: amino acid
       (D) TOPOLOGY: linear (ii) MOLECULE TYPE: peptide (xi) SEQUENCE DESCRIPTION: SEQ ID NO: 54:

Trp Cys Gly Pro Cys Lys Met Ile Lys Pro Phe Phe
 1               5                  10

(2) INFORMATION FOR SEQ ID NO: 55:

(i) SEQUENCE CHARACTERISTICS:
       (A) LENGTH: 13 amino acids
       (B) TYPE: amino acid
       (D) TOPOLOGY: linear (ii) MOLECULE TYPE: peptide (xi) SEQUENCE DESCRIPTION: SEQ ID NO: 55:

Leu Leu Phe Gly Pro Cys Ile Leu Asn Arg Leu Met Glu
 1               5                  10

PEPTIDES WITH IMMUNOMODULATORY EFFECTS

FIELD OF INVENTION

The present invention relates to non-antigen-specific immunomodulation, including both immunosuppression and immunostimulation.

BACKGROUND OF INVENTION

The immune system, when it is working properly, protects the individual from infection and from growth of cancers. In order to carry out these functions, it must be able to recognise and mount an attack against foreign antigens (including cancer-specific antigens), but not against self antigens present on normal cells throughout the body.

It is possible to stimulate the immune system in order to improve its level of protection. Vaccines, including single-protein antigens such as diptheria toxoid, are widely used to generate immunity against a specific antigen and thus a specific disease associated with that antigen. Where general stimulation of the immune system is desired, this can sometimes be achieved with nonspecific agents such as adjuvants, interleukins, interferons, and colony stimulating factors.

Occasionally, the immune system loses its critical ability to distinguish self from non-self. The resulting immunological assault on the individual's own tissues can take the form of autoimmune disease: for example, systemic lupus erythrematosis, Type 1 diabetes, or rheumatoid arthritis. In such a case, or alternatively where the individual is the recipient of a transplanted organ or tissue, suppression rather than stimulation of the immune response is desirable.

Non-specific down-regulation of the immune response is typically achieved by treatment with corticosteroids, azathioprine, cyclosporine, tacrolimus (FK506), rapamycin, or mycophenolate mofetil. Certain immunoglobulins, including the monoclonal antibody OKT3, have also been used for this purpose. Suppression of immunity against a specific antigen, called "tolerance induction", may also be possible. Methods that have been used for inducing tolerance against a particular antigen include intravenous or repeated topical administration of the antigen in dilute form, treatment with a very high dose of the antigen, and oral administration of the antigen.

SUMMARY OF THE INVENTION

It has now been found that certain peptides have activity as immunomodulators. Some of these peptides have been found to be immunoinhibitory, while others are immunostimulatory in effect. Experiments in animal models indicate that these peptides will be therapeuticly useful for the treatment of certain diseases, such as cancer and arthritis. Furthermore, and even more surprisingly, it has been found that oral administration of the peptides is a highly effective way to induce the desired immunomodulatory effect, even in the absence of any transport agents such as delivery vehicles, e.g., vesicular delivery systems which are designed to improve delivery to the mucosal epithelial cell lining of the gut. In addition, it has also been found that the amount of peptide required to produce the therapeutic effect by oral delivery can be significantly lower than that required to produce a similar effect when the peptide is delivered otherwise, e.g., by parenteral injection.

According to the present invention there is provided a purified physiologically active peptide comprising at least two cysteine amino acid residues, said two residues being aligned contiguous one to the other or separated by no more than one amino acid, the peptides being absorbable by the epithelial cell lining in a mammal resulting in a modulated immune response and thereby a therapeutic effect against disease.

The peptides are made up of amino acid residues independently selected from amino acid residues having aliphatic side chains, aliphatic hydroxyl side chains, basic side chains, acidic side chains, secondary amino groups, amide side chains, and sulphur containing side chains. Peptides of the invention must be physiologically active in the sense that they must be capable of inducing a modulated immune response and thereby a therapeutic effect against disease. Suitable amino acids may be independently selected from the groups comprising naturally and non-naturally occurring amino acid residues. Examples of naturally occurring amino acid residues include isoleucine (Ile), leucine (Leu), alanine (Ala), arginine (Arg), asparagine (Asn), aspartic acid (Asp), cysteine (Cys), glutamine (Gln), glutamic acid (Glu), glycine (Gly), lysine (Lys), phenyl alanine (Phe), proline (Pro), serine (Ser), threonine (Thr), tryptophan (Trp), tyrosine (Tyr), methionine (Met), valine (Val) and histidine (His). Thus, peptides of the invention can include additional cysteine residues either adjacent to or remote from the at least two cysteine amino acid residues mentioned hereinabove. Naturally, the skilled addressee will appreciate that naturally occurring amino acid residues means those amino acid residues which are found in peptides and/or proteins of living organisms. The skilled addressee will also appreciate that such naturally occurring amino acid residues may be present in peptides of the invention in chemically modified forms eg including added protecting groups such as ethyl, trityl (Trt), allyl, t-butyl and the like. Naturally, the skilled addressee will appreciate that any protecting group(s) which may be present on the peptides of the invention should be such so as not to substantially interfere with the immunomodulatory properties thereof and hence therapeutic effect thereof.

Purified peptides of the invention can be made synthetically, for example by chemical means, or through the use of recombinant DNA technology. Alternatively, peptides of the invention can be isolated from polypeptides or proteins and the like.

A peptide of the invention may take the form of a dimer consisting of two like or two dissimilar peptide monomers linked to each other by way of sulphur to sulphur bonds between at least one of the at least two cysteine amino acid residues of the first peptide monomer and at least one of the at least two cysteine amino acid residues of a second peptide monomer. In an aspect of the invention, the peptide monomers will be linked one to the other through sulphur to sulphur bonds between the at least two cysteine amino acid residues of the first peptide monomer and the at least two cysteine amino acid residues of the second peptide monomer. Dimers of the present invention may be in parallel form ie two peptide monomers aligned parallel one to the other such that both the peptide monomers are readable in one direction eg from the N-terminal to C-terminal direction. The peptide monomers making up the dimer may or may not be the same length. Preferably, the peptide monomers are the same length and the N- and C-terminal amino acid residues of one monomer are located adjacent to the N- and C-terminal amino acid residues of the second peptide monomer. Alternatively, a dimer of the present invention may be in anti-parallel form. That is to say, a first monomer read from the N-terminal amino acid residue to the C-terminal amino acid residue is aligned against a second monomer which is read from the C-terminal amino acid residue to the N-terminal amino acid residue ie in the opposite direction to that of the first peptide monomer; the two peptide monomers being linked through sulphur to sulphur bonds via the cysteine amino acid residues as described above for parallel or anti-parallel dimers of the invention. Where the two peptide monomers forming a peptide dimer of the invention are dissimilar one to the other, the dimer is referred to as an heterodimer. An heterodimer can be in parallel or anti-parallel form. Thus, a heterodimer can be composed of two peptide monomers of the same length, differing, for example, in the substitution of an amino acid residue having the L-form to an amino acid residue having the D-form. Alternatively, the lengths of the peptide monomers making up the dimer may be different. Preferably, the first and second peptide monomers making up a dimer of the present invention are the same.

Peptides of the invention also include monomers wherein the at least two contiguously aligned or spaced apart essential cysteine amino acid residues are linked through disulphide bridges. The monomers can be linear or cyclic. Preferably, the monomers are linear.

Administration of peptides of the invention by way of, for example, oral administration, intra-tracheal, nasal or parenteral administration gives rise to a measurable modulated immune response, as indicated in the examples herein.

"Epithelial cell lining" is defined as being the cell lining and associated cells thereto which covers the internal and external surfaces of the body, including the lining of vessels and other small cavities. For the purposes of the present invention the epithelial cell lining is regarded as being at least one cell layer in depth and as many as several cell layers deep. Cells included within the ambit of "epithelial cell lining" also includes those cells and specialised lymphoid tissues which are located in or associated with the said epithelial cell lining and which influence the immune response such as T-lymphocytes, B-lymphocytes, enterocytes, NK-cells, monocytes, dendritic cells and cells comprising mucosal associated lymphoid tissue (MALT), such as Peyer's patches and the like. Thus, the skilled addressee will appreciate that so-called migratory cells, such as T- and B-lymphocytes which can be regarded as transient resident cells of the epithelial cell lining as defined above are included within the ambit of the definition of epithelial cell lining. The peptides of the invention may be absorbed by the epithelial cell lining in a passive or active sense. For example, the peptides may be absorbed on the cell surface, or actively or passively taken up by cells located on the lumen surface side of the epithelial cell lining, or they may pass between cells located on the lumen surface side of the epithelial cell lining and are taken up by cells located deeper in the epithelial cell lining eg T-lymphocytes or Peyer's patches. The skilled addressee will also appreciate that "absorption" as defined herein also includes the situation wherein peptides of the invention initiate an immune response by interacting with cell surface receptors found in or on the membranes of certain specialised cells located in the epithelial cell lining, such as on enterocytes, and intra-epithelial lymphocytes, without physically penetrating the epithelial cell lining. Thus, the skilled addressee will understand that peptides of the invention may interact with, bind to, pass through or penetrate the epithelial cell lining.

The peptides of the invention are preferably administered by oral, nasal, or intra-tracheal administration in oral, nasal or intra-tracheal dosage forms. It has been found that the amount of a peptide of the invention required to produce a given therapeutic effect when orally administered can be significantly lower than that required to produce the same effect via other types of administration, such as parenteral administration.

In a further aspect of the invention there is provided an oral dosage form comprising an immunomodulatory peptide comprising at least two cysteine amino acid residues said two residues being aligned contiguous one to the other or separated by no more than one amino acid residue, the peptide being absorbable by the epithelial cell lining of the gastrointestinal tract in a mammal resulting in a modulated immune response and thereby a therapeutic effect against disease. The peptide can be in the form of a monomer or a dimer.

In a further aspect of the invention there is provided an oral dosage form comprising at least one immunomodulatory peptide each of which comprises at least two cysteine amino acid residues, said two cysteine residues being aligned contiguous one to the other or separated by no more than one amino acid residue, the at least one peptide being absorbable by the epithelial cell lining of the gastrointestinal tract in a mammal resulting in a modulated immune response and thereby a therapeutic effect against disease wherein the amount of the at least one orally administered peptide needed to induce an observable level of modulated immune response in a mammal is less than the amount of the same at least one peptide administered parenterally and needed to achieve a similar observable level of modulated immune response in the said mammal.

In a further aspect of the invention there is provided a nasal dosage form an immunomodulatory peptide comprising at least two cysteine amino acid residues, said two residues being aligned contiguous one to the other or separated by no more than one amino acid residue, the peptide being absorbable by the epithelial cell lining of the nasal passages in a mammal resulting in a modulated immune response and thereby a therapeutic effect against disease.

In a further aspect of the invention there is provided a nasal dosage form comprising at least one immunomodulatory peptide each of which comprises at least two cysteine amino acid residues, said two cysteine amino acid residues being aligned contiguous one to the other or separated by no more than one amino acid residue, the peptide being absorbable by the epithelial cell lining of the nasal passages in a mammal resulting in a modulated immune response and thereby a therapeutic effect against disease wherein the amount of the nasally administered peptide needed to induce an observable level of modulated immune response in a mammal is less than the amount of the same peptide administered parenterally and needed to achieve a similar observable level of modulated immune response in the said mammal.

In a further aspect of the invention there is provided an intra-tracheal dosage form comprising an immunomodulatory peptide comprising at least two cysteine amino acid residues said two residues being aligned contiguous one to the other or separated by no more than one amino acid residue, the peptide being absorbable by the epithelial cell lining of the lung in a mammal resulting in a modulated immune response and thereby a therapeutic effect against disease.

In a further aspect of the invention there is provided an intra-tracheal dosage form comprising at least one immunomodulatory peptide each of which comprises at least two cysteine amino acid residues said two cysteine residues being aligned contiguous one to the other or separated by no more than one amino acid residue, the at least one peptide being absorbable by the epithelial cell lining of the lung in a mammal resulting in a modulated immune response and thereby a therapeutic effect against disease wherein the amount of the at least one intra-tracheally administered peptide needed to induce an observable level of modulated immune response in a mammal is less than the amount of the same at least one peptide administered parenterally and needed to achieve a similar observable level of modulated immune response in the said mammal.

Peptides of the invention can be of any length provided that they are capable of inducing a modulated immune response and a therapeutic effect thereby. Generally, peptides of the invention are short peptides of from 4 amino acid residues up to about 30 amino acid residues in length. Preferably, the peptides are from 4 amino acid residues to about 20 amino acid residues in length. More preferably, the peptides of the invention are from 4 to 15 amino acids in length (e.g. 4 to 10 or 4 to 9), and, most preferably, from 4 to 7 amino acids in length. For example, the peptide can be 4, 5, 6, 7, or 8 amino acid residues in length, with or without protecting groups.

The peptides of the invention may or may not be associated with transport agents as defined herein. Preferably, the peptides of the invention are administered in a "naked" form ie free from added transport agents. Added transport agents are those with which the peptides of the invention are intentionally placed in contact or in association either before, during or immediately after administration and which may serve to improve absorption and/or improve the stability of the peptide.

Thus, in one preferment there is provided a purified physiologically active peptide free from added transport agents of from 4 to 15 amino acid residues in length comprising two cysteine amino acid residues, said residues being aligned contiguous one to the other or separated by no more than one amino acid residue, the said peptide being absorbable by the epithelial cell lining in a mammal resulting in a modulated immune response and thereby a therapeutic effect against disease. The peptide may be in the form of a monomer or dimer of the same or different peptides.

Suitable peptides of the invention will now be described with reference to the following formula:

Formula (I)

$$(A)_n\text{—X—Cys—Cys—Y—}(B)_m \qquad (I)$$

wherein

Each A is independently selected from H, a protecting group (for example, ethyl, trityl (Trt), allyl, and t-butyl), or at least one amino acid residue independently selected from the group of amino acid residues having aliphatic side chains, aliphatic hydroxyl side chains, basic side chains, acidic side chains, secondary amino groups, amide side chains, aromatic side chains, and sulphur containing side chains;

n is a whole integer selected from the group consisting of the set 1 to 11;

X is selected from the group consisting of NH, and the group of amino acid residues having secondary amino groups, amide side chains, and aliphatic side chains. Preferably, X is selected from the group Gly, Pro, Gln, Ile, Val, Asp, Leu, Glu, Ala, or NH.

Y is selected from consisting of NH, the group of amino acid residues having secondary amino groups, aliphatic side chains, acidic side chains, aliphatic hydroxyl side chains, aromatic side chains, and amide side chains. Preferably, Y is selected from the group Pro, Gly, Leu, Glu, Val, Ile, Ser, Phe, Tyr, Thr, Asp, Gln or NH;

Each B is independently selected from the group consisting of H, OH, $NH_2$, a protecting group, such as ethyl, trityl (Trt), allyl or t-butyl, or at least one amino acid residue selected from the group of amino acid residues having aliphatic side chains, aliphatic hydroxyl side chains, basic side chains, acidic side chains, secondary amino groups, amide side chains, aromatic side chains, and sulphur containing side chains;

m is a whole integer selected from the group consisting of the set 1 to 11;

with the proviso that when A is not at least one amino acid residue, n is 1 and when B is not at least one amino acid residue, m is 1; and the entire peptide sequence contains no more than 15 amino acid residues.

When A and/or B represent an amino acid residue or a sequence of amino acid residues, the amino acid residue or sequence of amino acid residues can include naturally occurring amino acid residues, such as those described hereinabove or analogues thereof or can include non-naturally occurring amino acid residues, such as synthetic amino acid residues and analogues thereof, or amino acid residues or sequences of amino acid residues including both naturally occurring amino acid residues and/or analogues thereof and non-naturally occurring amino acid residues and/or analogues thereof.

The skilled addressee will also appreciate that included within the scope of Formula (I) are peptides in which intramolecular disulphide bridges are present between the two Cys amino acid residues. Such peptides represent an oxidised form of peptides of Formula (I). The skilled addressee will also appreciate that the peptides of Formula (I) can be in the form of homodimers or heterodimers which may be in parallel or anti-parallel form. Such homodimers or heterodimers are comprised of monomers of Formula (I) and can be linked through sulphur to sulphur bonds via the cysteine residues.

Also included within the ambit of the invention are pharmaceutically acceptable salts of peptides of Formula (I) or physiologically functional derivatives thereof together with a pharmaceutically acceptable carrier therefor.

Preferred peptides of the invention according to Formula (I) are those wherein:

X is Gly and Y is Gly;
X is Pro and Y is Pro;
X is Pro and Y is Val;
X is Ile and Y is Leu;
X is Pro and Y is Glu;
X is Glu and Y is Tyr;
X is Pro and Y is Phe;
X is Glu and Y is Phe;
X is Ala and Y is Val;
X is Val and Y is Ile;
X is Gln and Y is Ser;
X is Ile and Y is Thr;
X is Leu and Y is Asp;
X is Asp and Y is Ile;
X is Leu and Y is Gln;
X is Gly and Y is Asn;
X is Gly and Y is Pro; and
X is Ala and Y is Gly;

and wherein A and B are as defined above.

More preferred peptides according to Formula (I) of the invention are:

Gly-Pro-Cys-Cys-Pro-Gly (SEQ ID NO:20);
Ala-Pro-Cys-Cys-Val-Pro (SEQ ID NO:21);
Lys-Pro-Cys-Cys-Glu-Arg (SEQ ID NO:22);
Pro-Asp-Cys-Cys-Ile-Pro (SEQ ID NO:23);
Ac-Ala-Pro-Cys-Cys-Val-Pro (SEQ ID NO:21);
Arg-Cys-Ser-Cys-Cys-Asn (SEQ ID NO:37);
Pro-Gly-Cys-Cys-Gly-Pro (SEQ ID NO:24);

```
Pro-Gly-Cys-Cys-Gly-Pro  (SEQ ID NO:24);
         |___|
Gly-Pro-Cys-Cys-Pro-Gly  (SEQ ID NO:20);
         |___|
Trp-Pro-Cys-Cys-Pro-Trp  (SEQ ID NO:25);
         |___|
Val-Ile-Cys-Cys-Leu-Thr  (SEQ ID NO:26);
         |___|
Thr-Pro-Cys-Cys-Phe-Ala  (SEQ ID NO:27);
         |___|
Glu-Glu-Cys-Cys-Phe-Tyr  (SEQ ID NO:28);
         |___|
Lys-Leu-Cys-Cys-Asp-Ile  (SEQ ID NO:29);
         |___|
Lys-Glu-Cys-Cys-Tyr-Val  (SEQ ID NO:30);
         |___|
Ala-Pro-Cys-Cys-Glu-Ser  (SEQ ID NO:48);
         |___|
Pro-Ala-Cys-Cys-Gly-Pro  (SEQ ID NO:49);
         |___|
Pro-Gly-Cys-Cys-Gly-Pro  (SEQ ID NO:24);
         |   |
Pro-Gly-Cys-Cys-Gly-Pro  (SEQ ID NO:24);
```

More preferred peptides according to Formula (I) of the invention are the peptides:
Gly-Pro-Cys-Cys-Pro-Gly (SEQ ID NO:20);
Pro-Gly-Cys-Cys-Gly-Pro (SEQ ID NO:24);
Ala-Pro-Cys-Cys-Val-Pro (SEQ ID NO:21);
Lys-Pro-Cys-Cys-Glu-Arg (SEQ ID NO:22);
Arg-Cys-Ser-Gly-Cys-Cys-Asn (SEQ ID NO:37);

```
Gly-Pro-Cys-Cys-Pro-Gly  (SEQ ID NO:20);
         |___|
Pro-Gly-Cys-Cys-Gly-Pro  (SEQ ID NO:24);
         |___|
Val-Ile-Cys-Cys-Leu-Thr  (SEQ ID NO:26);
         |___|
Pro-Ala-Cys-Cys-Gly-Pro  (SEQ ID NO:49);
Pro-Gly-Cys-Cys-Gly-Pro  (SEQ ID NO:24)
         |   |
Pro-Gly-Cys-Cys-Gly-Pro  (SEQ ID NO:24)
```

It is to be understood that the amino acid residues located at the N and C terminals respectively of the above peptides do not contain modifications thereto.

Formula (II)

$$(A)_n\text{—}X\text{—}Cys\text{—}Z\text{—}Cys\text{—}Y\text{—}(B)_m \quad\quad (II)$$

wherein

Each A is independently selected from the group consisting of H, a protecting group such as ethyl, trityl (Trt), allyl or t-butyl, or at least one amino acid residue selected from the group of amino acids in either L- or D-form having aliphatic side chains, aliphatic hydroxyl side chains, basic side chains, acidic side chains, secondary amino groups, amide side chains, and sulphur containing side chains;

n is a whole integer selected from the group consisting of the set 1 to 10;

X is selected from the group consisting of NH, and the group of amino acid residues having aliphatic side chains, secondary amino groups, acidic side chains, aromatic side chains, and amide side chains. Preferably, X is selected from the group consisting of Gly, Pro, Gln, Ile, Val, Asp, Leu, Glu, Ala, Lys or NH;

Z is selected from group consisting of amino acid residues having aliphatic side chains, aliphatic hydroxyl side chains, and basic side chains. Preferably, Z is selected from the group Ile, Gly, Thr, Ala, and Lys. Y is selected from the group consisting of amino acid residues having amide side chains, basic side chains, aliphatic side chains, acidic side chains, and secondary amino groups. Preferably, Y is selected from the group consisting of Pro, Gly, Glu, Val, Gln and Arg;

B is independently selected from the group consisting of H, OH, $NH_2$, a protecting group such as ethyl, trityl (Trt), allyl or t-butyl or at least one amino acid residue selected from the group of amino acid residues having aliphatic side chains, aliphatic hydroxyl side chains, basic side chains, acidic side chains, secondary amino groups, amide side chains, and sulphur containing side chains;

m is a whole integer selected from the set 1 to 10; with the proviso that when A is not at least one amino acid residue, n is 1, and when B is not at least one amino acid residue, m is 1; and each peptide sequence contains no more than 15 amino acid residues.

As for Formula (I), the skilled addressee will appreciate that when A and/or B represent an amino acid residue or sequences of amino acid residues, the amino acid residue or a sequence of amino acid residues can include naturally occurring amino acid residues, such as those described hereinabove or analogues thereof or can include non-naturally occurring amino acid residues, such as synthetic amino acid residues and analogues thereof, or amino acid residues of sequences of amino acid residues including both naturally occurring amino acid residues and/or analogues thereof and non-naturally occurring amino acid residues and/or analogues thereof.

The skilled addressee will also appreciate that included within the scope of Formula (II) are peptides in which intramolecular disulphide bridges between the two contiguously aligned or spaced apart Cys amino acid residues are present. Such peptides represent an oxidised form of peptides of Formula (II).

The skilled addressee will also appreciate that the dimers of Formula (II) may be in parallel or anti-parallel form and may include heterodimers, and can be linked through sulphur to sulphur bonds via the cysteine amino acid residues. Also included within the ambit of the invention are pharmaceutically acceptable salts of peptides of Formula (II) or physiologically functional derivatives thereof together with a pharmaceutically acceptable carrier therefor.

Preferred peptides of the invention according to Formula (II) include the following:
Val-Cys-Ile-Cys-Gln (SEQ ID NO:50);
Val-Cys-Gly-Cys-Arg (SEQ ID NO:40);
Asp-Cys-Ile-Cys-Gln (SEQ ID NO:54);
Ile-Cys-Thr-Cys-Glu (SEQ ID NO:52);
Phe-Cys-Ile-Cys-Lys (SEQ ID NO:36);
Ala-Cys-Lys-Cys-Gln (SEQ ID NO:55);

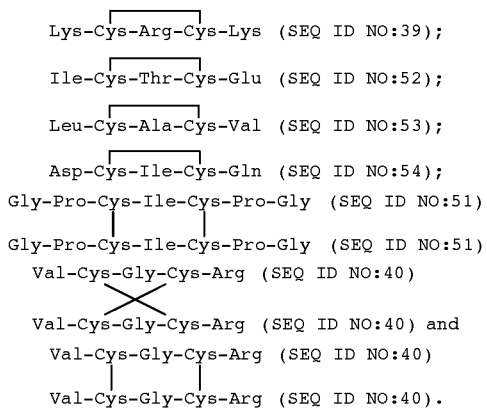

The peptides of the invention can be administered with or without transport agents. Preferably, peptides of the invention are administered orally, intra-tracheally, nasally, or systemically free from added transport agents. More preferably, the peptides of the invention are administered intra-tracheally, nasally, or orally. Most preferably, the peptides of the invention are administered orally. "Transport agents" includes added means for delivery such as vesicular delivery systems, micro particles, liposomes, and like systems which are designed to carry drugs (for example, peptides) to the epithelial cell lining or endothelial cell lining. "Transport agents" also includes chemicals or additional peptide sequences which may form an association with, or are fused to, or are complexed with the peptides and which help to maintain physiological integrity of peptide sequences of the invention, for example, presenting the peptides in a prepro- or pro-form or fusing the peptides to carrier proteins, for example glucosyl transferase, or complexed to chemical agents, such as cyclodextrins and the like. Preferably, peptides of the invention are administered to the recipient as free peptides along with the usual adjuvants, excipients and diluents commonly found in pharmaceutical formulations. Thus, peptides of the invention can be delivered by oral or systemic administration in simple oral or systemic formulations comprising adjuvants, diluents and excipients commonly employed in oral and systemic dosage forms. Preferably, the peptides are administered in an oral dosage form free from added transport agents.

Mucosal associated lymphoid tissue (MALT) is also found in the epithelial cell linings of the gastrointestinal tract, that is, esophagous, stomach, duodenum, ileum, and colon; bronchiole linings in the lung; and in the linings of the nasal passages. Without the intention of being bound by theory, it is thought that the peptides of the invention interact with MALT and thereby set in train a sequence of immunomodulating events which results in a therapeutic effect against certain diseases.

The immunomodulatory response can be immunoinhibitory or immunostimulatory in effect. The immunomodulatory response has been shown to be indicative for therapy against cancer. The peptides of the invention having an immunomodulatory effect are indicated as being advantageous in the treatment of cancers of mesenchymal origin such as sarcoma, for example, fibrosarcoma, myxosarcoma, liposarcoma, chondrosarcoma, osteogenic sarcoma or chordosarcoma, angiosarcoma, endotheliosarcoma, lymphangiosarcoma, synoviosarcoma or mesotheliosarcoma; leukemias and lymphomas such as granulocytic leukemia, monocytic leukemia, lymphocytic leukemia, malignant lymphoma, plasmocytoma, reticulum cell sarcoma or Hodgkins disease; sarcomas like leiomysarcoma or rhabdomysarcoma, tumours of epithelial origin (Carcinomas) such as squamous cell carcinoma, basal cell carcinoma, sweat gland carcinoma, sebaceous gland carcinoma, adenocarcinoma, papillary carcinoma, papillary adenocarcinoma, cystadenocarcinoma, medullary carcinoma, undifferentiated carcinoma, bronchogenic carcinoma, melanoma, renal cell carcinoma, hepatoma-liver cell carcinoma, bile duct carcinoma, cholangiocarcinoma, papillary carcinoma, transitional cell carcinoma choriocarcinoma, semonoma or embryonal carcinoma; and tumours of the central nervous system like glioma, meningoma, medulloblastoma, schwannoma or ependymoma. Peptides of the invention are indicated on the basis of their activity for the treatment of malignancies such as melanoma, mammary carcinoma, gastrointestinal carcinoma such as colonic carcinomas, glioma, bladder carcinoma and squamous cell carcinoma of the neck and head region. Furthermore, peptides producing an immunomodulatory effect in tests described herein are indicated for therapy in the treatment of acute and/or chronic infections associated with autoimmune disease and autoimmune disease per se such as non-obese diabetes, systemic lupus erythematosus, sclerodermia, Sjögren's syndrome, dermatomyositis or multiple sclerosis, rheumatoid arthritis, artheriosclerosis, and psoriasis, asthma, rhinitis, fibrosis, chronic bronchitis, hepatitis, post-infectious anergy, acquired immune deficiency diseases such as AIDS, and post traumatic immunological anergy.

Moreover, the peptides according to the present invention, being immunomodulatory in action, may be advantageously employed as adjuvants in various forms of vaccine preparations and in formulations designed to inhibit rejection of organs in transplants.

In another aspect of the invention, there is provided a method of inducing a modulated immune response in a mammal which comprises administering to the epithelial cell lining of the mammal a dose of a purified physiologically active, immunomodulatory peptide comprising at least two cysteine amino acid residues, said two residues being aligned contiguous one to the other or separated by no more than one amino acid residue, enough to induce said modulated immune response and thereby a therapeutic effect.

In a further aspect of the invention there is provided a method of inducing a modulated immune response in a mammal which comprises (1) identifying a mammal in need of modulation of its immune response and (2) administering to at least one epithelial cell lining of the mammal a dose of a physiologically active, purified, peptide free from added transport agents of from 4 to 15 amino acid residues in length comprising two cysteine amino acid residues said residues being aligned contiguous one to the other or separated by no more than one amino acid residue, enough to induce said immunomodulatory response and thereby a therapeutic effect. Preferably, the epithelial cell lining to which the peptide is administered is the epithelial cell lining of the gastrointestinal tract. Most preferably, the peptide is administered to the MALT.

In a preferment there is provided a method of inducing a modulated immune response in a mammal which comprises administering to MALT of the mammal a dose of a physiologically active peptide of Formula (I), said peptide being free from added transport agents and being sufficient to induce said modulated immune response and thereby a therapeutic effect. The peptide can be in monomer or dimer form.

In a preferment there is provided a method of inducing a modulated immune response in a mammal which comprises administering to MALT of the mammal a dose of a physiologically active peptide of Formula (II), said peptide being free from added transport agents and being sufficient to induce said immunomodulatory response and thereby a therapeutic effect. The peptide can be in monomer or dimer form.

In a further aspect of the invention there is provided use of a physiologically active peptide of from 4 to 15 amino acid residues in length comprising two cysteine residues being aligned contiguous one to the other or separated by no more than one amino acid residue, said peptide being free from added transport agents, in the preparation of a medicament suitable for the treatment of disease. Particular forms of cancer which may be treated with peptides of the invention are listed hereinabove. In a preferment, there is provided use of a physiologically active peptide of Formula (I) free from added transport agents in the preparation of a medicament suitable for the treatment of disease, in particular cancer and rheumatoid arthritis. Also encompassed as a further aspect of the invention is use of a physiologically active peptide of Formula (II) free from added transport agents in the preparation of a medicament suitable for the treatment of disease, in particular cancer and rheumatoid arthritis.

In a further embodiment of the invention there is provided a method of making a peptide of the invention by a chemical process in which individual amino acid residues or fragments of peptides of the invention are joined to form peptide bonds and wherein protecting groups are employed at the beginning and/or end of the process.

In another embodiment of the invention there is provided as a further alternative aspect of the invention a physiologically active peptide free from added transport agents of from 4 to 15 amino acid residues in length comprising two cysteine residues said amino acid residues being separated by no more than one amino acid residue for use in therapy, for example, in cancer or rheumatoid arthritis therapy. In a preferment, there is provided a peptide of Formula (I) or Formula (II) for use in therapy, for example in cancer therapy or rheumatoid arthritis therapy.

The amount of peptides of Formula (I) or Formula (II) which are required in cancer or rheumatoid arthritis therapy will, of course, vary and is ultimately at the discretion of the medical or veterinary practitioner. The factors to be considered include the condition being treated, the route of administration, and nature of the formulation, the mammal's body weight, surface area, age, and general condition and the particular peptide to be administered. A suitable effective dose of peptides of the invention generally lies in the range of from about 0.0001 $\mu$mol/kg to about 1000 $\mu$mol/kg body weight, preferably from about 0.003 to about 300 $\mu$mol/kg body weight, e.g. in the range of from about 0.001 to 100 $\mu$mol/kg bodyweight, for example, 0.03 to 3.0 $\mu$mol/kg bodyweight. The total dose may be given as a single dose or multiple doses, e.g two to six times per day. For example, for a 75 kg mammal (e.g. a human) the dose range would be about 2.25 $\mu$mol/kg/day to 225 $\mu$mol/kg/day and a typical dose could be about 100 $\mu$mol of peptide. If discrete multiple doses are indicated treatment might typically be 25 $\mu$mol of a peptide of the invention given up to 4 times per day. In an alternative administrative regimen, peptides of the invention may be given on alternate days or even once or twice a week. The skilled addressee will appreciate that an appropriate administrative regimen would be at the discretion of the physician or veterinary practitioner.

Whilst it is possible for the active peptide to be administered alone, it may be preferable to present the active peptide in a pharmaceutical formulation. Formulations of the present invention, for medical use, comprise a peptide of Formula (I) or Formula (II) or a salt thereof together with one or more pharmaceutically acceptable carriers and optionally other therapeutic ingredients. The carrier(s) should be pharmaceutically acceptable in the sense of being compatible with the other ingredients of the formulation and substantially non-deleterious to the recipient thereof. The skilled addressee will appreciate that free acid addition salts (e.g. hydro-halo salts) of peptides referred to herein as well as base salts are encompassed within the ambit of the invention. Most preferably the salts will be pharmaceutically acceptable.

Suitable acid addition salts include those formed from hydrochloric, hydrobromic, nitric, perchloric, sulphuric, citric, tartaric, phosphoric, lactic, benzoic, glutamic, oxalic, aspartic, pyruvic, acetic, succinic, fumaric, maleic, oxaloacetic, isethionic, stearic, phthalic, methanesulphonic, p-toluene sulphonic, benzenesulphonic, lactobionic, and glucuronic acids. Suitable base salts include inorganic base salts such as alkali metal (e.g. sodium and potassium salts and alkaline earth metal (e.g. calcium) salts; organic base salts e.g. phenylethylbenzylamine, dibenzylethylenediamine, ethanolamine and diethanolamine salts; and amino acid salts e.g. lysine and arginine. Most preferably, the salts will be pharmaceutically acceptable.

The present invention, therefore, further provides a pharmaceutical formulation comprising a peptide of Formula (I) or Formula (II) together with a pharmaceutically acceptable carrier therefor.

Naturally, the skilled addressee will appreciate that any pharmaceutical formulation comprising a peptide of Formula (I) can include more than one peptide of Formula (I). Thus, a pharmaceutical formulation may comprise at least two peptides of Formula (I) or (II) or a cocktail of peptides of Formula (I) or (II). In an alternative, the pharmaceutical formulation may comprise at least two peptides, at least one being selected from Formula (I) and at least one being selected from Formula (II), and may comprise a cocktail of peptides selected from Formulae (I) and (II).

There is also provided a method for the preparation of a pharmaceutical formulation comprising bringing into association a peptide of the invention, for example, at least one peptide of Formula (I) and/or at least one peptide of Formula (II) or a physiologically functional derivative thereof, and a pharmaceutically acceptable carrier therefor.

The peptides of the invention and physiologically functional derivatives thereof may be administered by any route appropriate to the condition to be treated, suitable routes including oral, intra-tracheal, rectal, nasal, topical (including buccal and sublingual), vaginal, and parenteral (including subcutaneous, intramuscular, intravenous, intradermal, intrathecal, intraperitoneal, and epidural). It will be appreciated that the route may vary with, for example, the condition of the recipient. Preferred formulations are those suitable for oral, nasal or intra-tracheal administration. Most preferred formulations are those suitable for oral administration.

Formulations for topical administration in the mouth include lozenges comprising the peptide(s) in a flavoured basis, usually sucrose and acacia and tragacanth; pastilles comprising the active ingredient in an inert base such as gelatin and glycerin, or sucrose and acacia; and mouth washes comprising the peptide(s) in a suitable liquid carrier.

Formulations of the present invention suitable for oral administration may be presented as discrete units such as capsules, cachets, tablets, lozenges comprising the peptide (s) in a flavoured base, usually sucrose and acacia and tragacanth; pastilles comprising the active ingredient(s) in an inert base such as gelatin and glycerin, or sucrose and acacia; and mouth washes comprising the active ingredient (s) in a suitable liquid carrier. Each formulation generally contains a predetermined amount of the active peptide(s); as a powder or granules; or a solution or suspension in an aqueous or non-aqueous liquid such as a syrup, an elixir, an emulsion or draught and the like.

A tablet may be made by compression or moulding, optionally with one or more accessory ingredients. Compressed tablets may be prepared by compressing in a suitable machine the active peptide(s) in a free-flowing form such as a powder or granules, optionally mixed with a binder, (eg povidone, gelatin, hydroxypropylmethyl cellulose), lubricant, inert diluent, preservative, disintegrant (e.g. sodium starch glycollate, cross-linked povidone, cross-linked sodium carboxymethyl cellulose), surface active or dispersing agent. Moulded tablets may be made by moulding in a suitable machine a mixture of the powdered peptide (s) moistened with an inert liquid diluent. The tablets may optionally be coated or scored and may be formulated so as to provide slow or controlled release of the active ingredient therein using, for example, hydroxypropylmethyl cellulose in varying proportions to provide the desired release profile.

A syrup may be made by adding the active peptide(s) to a concentrated, aqueous solution of a sugar, for example, sucrose, to which may also be added any necessary ingredients. Such accessory ingredients) may include flavourings, an agent to retard crystallisation of the sugar or an agent to increase the solubility of any other ingredients, such as a polyhydric alcohol, for example, glycerol or sorbitol.

In addition to the aforementioned ingredients, the formulations of this invention may further include one or more accessory ingredient(s) selected from diluents, buffers, flavouring agents, binders, surface active agents, thickeners, lubricants, preservatives, (including antioxidants) and the like.

Emulgents and emulsion stabilisers suitable for use in the formulation of the present invention include Tween 60, Span 80, cetostearyl alcohol, myristyl alcohol, glyceryl monostearate and sodium lauryl sulphate.

The choice of suitable oils or fats for the formulation is based on achieving the desired therapeutic properties, since the solubility of the active compound in most oils likely to be used in pharmaceutical emulsion formulations is low. Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate, or a blend of branch-chained esters known as Crodamol CAP may be used, the last three being preferred esters. These may be used alone or in combination depending on the properties required. Alternatively, high melting point lipids such as white soft parafin and/or liquid parafin or other mineral oils can be used.

Formulations for rectal administration may be presented in any suitable form e.g. as a suppository with a suitable base comprising peptide(s) of the invention in admixture with a neutral fatty base, for example cocoa butter, or, for example in admixture with a salicylate, or in the form of solutions and suspensions. In an alternative, formulations in the form of gelatin rectal capsules comprising active peptide(s) of the invention in admixture with vegetable oil(s) or paraffin oil can be used.

Formulations suitable for nasal administration wherein the carrier is a solid include a coarse powder having a particle size for example in the range 20 to 500 microns. Where the particle size relates to an active substance in particle form per se, the particle size may be in the range of from 2 to 500 microns. Coarse powder formulations can be administered by rapid inhalation through the nasal passage from a container of the powder held up close to the nose. Suitable formulations wherein the carrier is a liquid, for administration as for example a nasal spray or as nasal drops, include aqueous or oily solutions of the active ingredient. Thus, peptides of the invention may be formulated in pressurised metered dose inhalers or dry powder inhalers for oral or nasal inhalation or in liquid formulations for nebulisation. The active peptide(s) is micronised or otherwise processed to a particle size suitable for inhalation therapy (mass median diameter <10 $\mu$m).

In the case of pressurised metered dose inhalers the micronised peptide(s) can be suspended in a liquefied propellant or a mixture of liquefied propellants. Such propellants can also, but not necessarily act as solvents. In either case, the micronised peptide(s) can be filled into a container equipped, for example with a metering valve.

Suitable propellants include those commonly employed in the art, such as, hydrofluoroalkanes (HFAs). The HFA propellants can be present in any mixture which is appropriate for delivering peptide(s) of the invention to MALT. Examples of suitable HFAs for use in the invention include tetrafluoroethane (e.g., propellant 134a (Hoechst)) and heptafluoropropane (e.g., propellant 227 (Hoechst)). Naturally, the skilled addressee will appreciate that appropriate concentrations of surfactants can also be present in such formulations, for example, sorbitan trioleate, lecithin, oleic acid and the like, the use of surfactants being to increase the physical stability of the peptide(s) preparation. The formulation can also contain solvents, such as ethanol, to improve the solubility of the peptide(s) in the chosen propellant.

Active peptides of the invention may be delivered through inhaling devices suitable for dry powder inhalation, such as portable inhaler devices and the like. In such dry powder formulations, the active peptide(s) of the invention can be used either alone or in combination with a carrier, such as lactose, mannitol, or glucose. The selection of carrier is not critical, provided that the physiological action of the peptide (s) of the invention is substantially unimpaired. Other additives may also be included in powder formulations as required e.g. to maintain stability etc. Again, such additives should be such so as not to substantially interfere with the physiological and hence therapeutic effect of the peptide(s) of the invention. The inhaling device can be of any type known in the art, such as a single dose inhaler having a predetermined dose or a multi-dose inhaler wherein the dose is measured by a metering unit within the inhaler or is delivered from an assembly of predetermined doses.

Formulations suitable for parenteral administration conveniently comprise a sterile aqueous preparation of the active compound which is preferably isotonic with the blood of the recipient. Such formulations suitably comprise a solution of a pharmaceutically and pharmacologically acceptable acid addition salt of a peptide(s) of the invention that is isotonic with the blood of the recipient.

Useful formulations also comprise concentrated solutions or solids containing peptide(s) of the invention which upon dilution with an appropriate solvent give a solution for parenteral administration as above.

The invention will now be illustrated by the following non-limiting examples.

1. Synthesis of Peptides

It is to be understood that where no group is shown at the N- and C-termii of peptides of that the N-terminal is in the amino form and that the C-terminal is in the carboxyl form.

The peptide numbering system in the following examples is that used in Table 1 which shows results obtained from Example 43.

EXAMPLE 1

Synthesis of Pro-Gly-Cys-Cys-Gly-Pro (SEQ ID NO:24)

Fmoc-proline coupled to a resin (1.11 g, 0.18 mmol/g, 0.20 mmol) consisting of a crosslinked polystyrene backbone grafted with polyethyleneglycol chains, functionalized with the linker p-carboxy-triphenylmethanol (Sheppard, R. C., Williams, B. J. Acid-labile Resin Linkage Agents for Use in Solid Phase Peptide Synthesis. Int. J. Peptide Protein Res. 1982, 20, 451–454) from Rapp Polymer was used for the synthesis. N-Fmoc-protected L-amino acid pentafluorophenyl esters used were purchased from Bachem and Millipore, and Cys was protected with a triphenylmethyl (Trt) group. DMF and 20% piperidine/DMF in peptide reagent quality was purchased from Millipore. The coupling reagent 1-hydroxybenzotriazole (HOBT) came from Fluka. Synthesis was performed on a Millipore 9050 Plus PepSynthesizer.

The C-terminal amino acid, Tentagel S trt-Pro-Fmoc (1.11 g, 0.18 mmol/g, 0.20 mmol) on resin (from Rapp Polymer) was allowed to swell in DMF for 30 minutes before adding the slurry to the column of the synthesizer. The synthesizer worked with consecutive deblocking, washing and coupling cycles consisting of 8 min recycling with 20% piperidine/DMF for each Fmoc-deblocking followed, after wash by activation of the $N^\alpha$-Fmoc-protected L-amino acid pentafluorophenyl ester (0.8 mmol) with HOBT (0.9 mmol). The activated amino acids were added to the column and recycled 30 minutes each. The synthesizer ended the synthesis with a deblocking of the N-terminal Fmoc-group and a final wash with DMF. The resulting peptide on the resin was transferred to a sintered glass funnel where it was washed twice with MeOH (2×10 ml) and three times with $CH_2Cl_2$ (3×10 ml). The resin was allowed to dry under vacuum over night after which the peptide was side chained deprotected and cleaved from the resin using ethanedithiol/TFA 5/95 (20 ml) at room temperature for 3 hours. The resin was filtered off and washed with 3×10 ml of acetic acid. The combined acidic fraction was evaporated after which the residue was triturated 3 times 10 with ether.

The crude peptide was dissolved in $H_2O/CH_3CN$ 1/1 and freeze dried. The resulting material was purified on HPLC using a Gilson 305 and 306 HPLC system with a Kromasil 100-5C18 25 cm×22 mm id reversed phase column (A=0.1% $TFA/H_2O$–B=0.1% $TFA/CH_3CN$: 5–80%/25 min; 10 ml/min, 220 nm). The combined HPLC fraction was freeze dried leaving 84 mg of the title compound. $MH^+$ (m/z)=533

EXAMPLE 2

Lys-Leu-Cys-Cys-Gln-Met (SEQ ID NO:32).

Lys-Leu-Cys-Cys-Gln-Met (SEQ ID NO:32; 39.6 mg, 54.7 μmol) was prepared following a similar protocol as per Example 1. Lys-Leu-Cys-Cys-Gln-Met (SEQ ID NO:32) was dissolved in 5% aqueous acetic acid (80 ml) and the pH of the solution was adjusted to 6 with ammonium carbonate. Dimethylsulfoxide (60 ml) was added and the mixture was stirred at room temperature for 24 hours. Upon completion, the reaction mixture was concentrated in vacuo until ca. 8 ml remained. The solution was purified by semipreperative HPLC (APEX Prep Sil ODS, 8 μm, 25 cm×20 mm i.d., eluted with a linear gradient of $CH_3CN$, 5–60% 50 min. in 0.1% aqueous TFA, flow rate 10 ml/min, UV detection at 220 nm) and then lyophilised to give the title peptide (19.7 mg, 50% as a white powder. HRMS (FAB+) Exact mass calculated for $C_{28}H_{51}N_8O_8S_3$: 723.299; found: 723.302.

EXAMPLE 3

Synthesis of Parallel Intermolecularly Oxidized Dimer

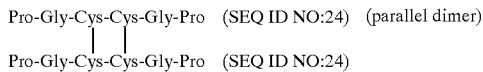

To prepare the parallel homodimer a single peptide chain with an Acm (acetamidomethyl) protecting group on one of the cysteines and with the other cysteine unprotected (Pro-Gly-Cys-Cys(Acm)-Gly-Pro; SEQ ID NO:24) was synthesized using the same protocol as per Example 1. The monomer was dimerized through oxidation of the free cysteines using the same protocol as per Example 2. The second disulfide bond was accomplished using the protocol of Ruiz-Gayo (Ruiz-Gayo et al., 1988, Tetrahedron Letters, 29, 3845–3848) in which the monoxidized dimer (100 mg, 83 μmol) was dissolved in MeOH (16 ml).

Freshly prepared 0.2 M $I_2/CH_3OH$ (8.2 ml, 1.64 mmol) was added and the mixture was stirred at room temperature for 2 hours. $H_2O$ (20 ml) was added after which 0.5 M ascorbic acid (aq) was slowly added to the mixture until the colour of the iodine disappeared. The mixture was carefully evaporated at room temperature to half volume. The crude product was lyophilized and then purified on HPLC.

EXAMPLE 4

Synthesis of Antiparallel Dimer

To prepare the antiparallel homodimer the general procedure of Ruiz-Gayo was used (Ruiz-Gayo et al., 1988, Tetrahedron Letters, 29, 3845–3848). Two single peptide chains each with an Acm (acetamidomethyl) protecting group on one of the cysteines and with the other cysteine unprotected ((Pro-Gly-Cys-Cys(Acm)-Gly-Pro (SEQ ID NO:24) and Pro-Gly-Cys(Acm)-Cys-Gly-Pro) (SEQ ID NO:24)) were synthesized using the same protocol as in Example 1. The unprotected cysteine on one of the monomers was activated with dithiopyridine through dissolving one of the monomers (62 μmol) in isopropanol/2 M acetic acid (50/50, 20 ml) and adding 2,2'-dithiopyridine (205 μmol dissolved in 15 ml of isopropanol/2 M acetic acid 50/50). The mixture was allowed to stir at room temperature overnight. The mixture was evaporated, then $CH_3CN$ (25 ml) was added and the mixture was evaporated once more. The remaining crude was triturated with ether (4×25 ml) and the resulting S-pyridyl derivative Pro-Gly-Cys(SPyr)-Cys(Acm)-Gly-Pro (SEQ ID NO:24) was used directly without any further purification. This activated derivative was reacted with the second peptide chain (62 μmol) through dissolving the activated chain in 0.01M ammonium acetate solution (50 ml, pH=6.5) and adding the other chain (dissolved in 17 ml 0.01 M ammonium acetate(aq)) and allowing the mixture to stir for 30 minutes. The reaction mixture was lyophilized and the crude product was purified on HPLC resulting in the monodisulfidedimer. The second disulfide bond was accomplished using the same protocol as in Example 3 with iodine in CH$_3$OH which, after purification on HPLC, resulted in the final product.

EXAMPLE 5

Synthesis of Gly-Pro-Cys-Cys-Pro-Gly (SEQ ID NO:20)

Synthesis was accomplished following a similar protocol as per Example 1.

EXAMPLE 6

Synthesis of Ala-Pro-Cys-Cys-Val-Pro (SEQ ID NO:21)

Synthesis was accomplished using a similar protocol as per Example 1.

EXAMPLE 7

Synthesis of Phe-Cys-Ile-Cys-Lys (SEQ ID NO:36)

Synthesis was accomplished using a similar protocol as per Example 1.

EXAMPLE 8

Synthesis of Lys-Pro-Cys-Cys-Glu-Arg (SEQ ID NO:22)

Synthesis was accomplished using a similar protocol as per Example 1.

EXAMPLE 9

Synthesis of Arg-Cys-Ser-Gly-Cys-Cys-Asn (SEQ ID NO:37)

Synthesis was accomplished using a similar protocol as per Example 1.

EXAMPLE 10

Synthesis of Intramolecularly Oxidized

Gly-Pro-Cys̄-Cȳs-Pro-Gly (SEQ ID NO:20).

Synthesis was accomplished using a similar protocol as per Example 2.

EXAMPLE 11

Synthesis of Intramolecularly Oxidized

Val-Ile-Cys̄-Cȳs-Leu-Thr (SEQ ID NO:26).

Synthesis was accomplished using a similar protocol as per Example 2.

EXAMPLE 12

Synthesis of Intramolecularly Oxidized

Lys-Leu-Cys̄-Cȳs-Asp-Ile (SEQ ID NO:29).

Synthesis was accomplished using a similar protocol as per Example 2.

EXAMPLE 13

Synthesis of Intramolecularly Oxidized

Thr-Pro-Cys̄-Cȳs-Phe-Ala (SEQ ID NO:27).

Synthesis was accomplished using a similar protocol as per Example 2.

EXAMPLE 14

Synthesis of Intramolecularly Oxidized

Lys-Glu-Cys̄-Cȳs-Tyr-Val (SEQ ID NO:30).

Synthesis was accomplished using a similar protocol as per Example 2.

EXAMPLE 15

Synthesis of Intramolecularly Oxidized

Lys-Cys̄-Arg-Cȳs-Lys (SEQ ID NO:39).

Synthesis was accomplished using a similar protocol as per Example 2.

EXAMPLE 16

Synthesis of Antiparallel Intermolecularly Oxidized Dimer

Val-Cys-Gly-Cys-Arg (SEQ ID NO:40)
Val-Cys-Gly-Cys-Arg (SEQ ID NO:40).

Synthesis was accomplished using a similar protocol as per Example 4.

EXAMPLE 17

Synthesis of Intramolecularly Oxidized

Pro-Gly-Cys-Cys-Gly-Pro (SEQ ID NO:24)

Synthesis was accomplished following a similar protocol as per Example 2.

EXAMPLE 18

Synthesis of Intramolecularly Oxidised

Trp-Pro-Cys-Cys-Pro-Trp (SEQ ID NO:25).

Synthesis was accomplished following a similar protocol as per Example 2.

EXAMPLE 19

Synthesis of Intramolecularly Oxidised

Leu-Leu-Phe-Gly-Pro-Cys-Cys-NH$_2$ (SEQ ID NO:41)

Synthesis was accomplished following a similar protocol as per Example 2.

EXAMPLE 20

Synthesis of Intramolecularly Oxidised

Glu-Glu-Cys-Cys-Phe-Tyr (SEQ ID NO:28)

Synthesis was accomplished following a similar protocol as per Example 2.

EXAMPLE 21

Synthesis of Pro-Val-Cys-Cys-Ile-Gly (SEQ ID NO:42)

Synthesis was accomplished following a similar protocol as per Example 1.

EXAMPLE 22

Synthesis of Intramolecularly Oxidised

Pro-Val-Cys-Cys-Ile-Gly (SEQ ID NO:42)

Synthesis was accomplished following a similar protocol as per Example 2.

EXAMPLE 23

Synthesis of Intramolecularly Oxidised

Ser-Gln-Cys-Cys-Ser-Leu (SEQ ID NO:43)

Synthesis was accomplished following a similar protocol as per Example 2.

EXAMPLE 24

Synthesis of Intramolecularly Oxidised

Ser-Ile-Cys-Cys-Thr-Lys (SEQ ID NO:44)

Synthesis was accomplished following a similar protocol as per Example 2.

EXAMPLE 25

Synthesis of Pro-Asp-Cys-Cys-Ile-Pro (SEQ ID NO:23)

Synthesis was accomplished following a similar protocol as per Example 1.

EXAMPLE 26

Synthesis of Leu-Ala-Cys-Cys-Val-Val (SEQ ID NO:45)

Synthesis was accomplished following a similar protocol as per Example 1.

EXAMPLE 27

Synthesis of

Pro-Gly-Cys-Cys-Pro-Gly (SEQ ID NO:46)

Synthesis was accomplished following a similar protocol as per Example 2.

EXAMPLE 28

Synthesis of Ac-Ala-Pro-Cys-Cys-Val-Pro (SEQ ID NO: 21)

Synthesis was accomplished following a similar protocol as per Example 1 with an additional methylation step in the end of the synthetic sequence on the Millipore 9050 PlusPep Synthesizer consisting of addition of 0.3 M N-Acetylimidazole in DMF to the resin and allowing the solution to circulate through the synthetic column for 2 hours followed by washing with DMF.

EXAMPLE 29

Synthesis of Lys-Glu-Cys-Cys-Tyr-Val (SEQ ID NO:30)

Synthesis was accomplished following a similar protocol as per Example 1.

EXAMPLE 30

Synthesis of Lys-Leu-Cys-Cys-Gln-Met (SEQ ID NO:32)

Synthesis was accomplished following a similar protocol as per Example 1.

EXAMPLE 31

Synthesis of

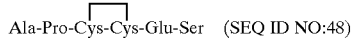 Ala-Pro-Cys-Cys-Glu-Ser (SEQ ID NO:48)

Synthesis was accomplished following a similar protocol as per Example 2.

EXAMPLE 32

Synthesis of

 Pro-Ala-Cys-Cys-Gly-Pro (SEQ ID NO:49)

Synthesis was accomplished following a similar protocol as per Example 2.

EXAMPLE 33

Synthesis of Val-Cys-Ile-Cys-Gln (SEQ ID NO:50)

Synthesis was accomplished following a similar protocol as per Example 1.

EXAMPLE 34

Synthesis of

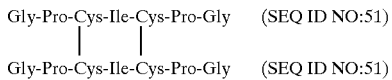
Gly-Pro-Cys-Ile-Cys-Pro-Gly (SEQ ID NO:51)
Gly-Pro-Cys-Ile-Cys-Pro-Gly (SEQ ID NO:51)

Synthesis was accomplished following a similar protocol as per Example 3.

EXAMPLE 35

Synthesis of Val-Cys-Gly-Cys-Arg (SEQ ID NO:40)

Synthesis was accomplished following a similar protocol as per Example 1.

EXAMPLE 36

Synthesis of

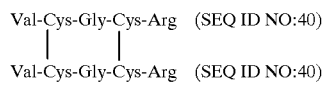
Val-Cys-Gly-Cys-Arg (SEQ ID NO:40)
Val-Cys-Gly-Cys-Arg (SEQ ID NO:40)

Synthesis was accomplished following a similar protocol as per Example 3.

EXAMPLE 37

Synthesis of Ile-Cys-Thr-Cys-Glu (SEQ ID NO:52)

Synthesis was accomplished following a similar protocol as per Example 1.

EXAMPLE 38

Synthesis of

 Ile-Cys-Thr-Cys-Glu (SEQ ID NO:52)

Synthesis was accomplished following a similar protocol as per Example 2.

EXAMPLE 39

Synthesis of

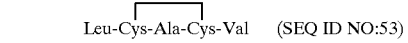 Leu-Cys-Ala-Cys-Val (SEQ ID NO:53)

Synthesis was accomplished following a similar protocol as per Example 2.

EXAMPLE 40

Synthesis of Asp-Cys-Ile-Cys-Gln (SEQ ID NO:54)

Synthesis was accomplished following a similar protocol as per Example 1.

EXAMPLE 41

Synthesis of

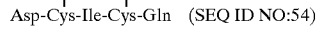 Asp-Cys-Ile-Cys-Gln (SEQ ID NO:54)

Synthesis was accomplished following a similar protocol as per Example 2.

EXAMPLE 42

Synthesis of Ala-Cys-Lys-Cys-Gln (SEQ ID NO:55)

Synthesis was accomplished following a similar protocol as per Example 1.

EXAMPLE 43

Delayed Type Hypersensitivity (DTH) Test

The ability of the peptides according to the invention to modulate immune responses can be illustrated by their effect in the delayed type hypersensitivity (DTH) test in mice. The DTH test is used to illustrate immunomodulation, the protocol for which is described, for example, by Carlsten H., et al (1986) Int. Arch. Allergy Appl. Immunol 81:322, herein incorporated by reference. The peptides were tested at one or more of the following dosages: 0.0003 µmol/kg, 0.003 µmol/kg, 0.03 µmol/kg, 0.3 µmol/kg, and 3.0 µmol/kg.

Male and female Balb/c mice were obtained from Bomholtsgaard (Denmark) with a weight of 18–20 grams each. 4-Ethoxymethylene-2-phenyloxazolin-5-one (OXA) (Sigma Chemicals) was used as the antigen in the DTH test.

The mice were sensitized, Day 0, by epicutaneous application of 150 µl of an absolute ethanol-acetone (3:1) solution containing 3% OXA on the shaved abdomen. Treatment with peptides 1 to 41 inclusive, or vehicle (phosphate buffer, pH 7.4, containing a mixture of Buffer A and Buffer B in the proportion 63%:37% B (Buffer A: $Na_2HPO_4$, 0.89 g/100 ml, EDTA 0.05 g/100 ml; Buffer B: $NaH_2PO_4$, 0.69 g/100 ml, EDTA 0.05 g/100 ml) was initiated by oral feeding immediately after sensitization and continued once daily (a.m) until Day 6. Seven days after sensitization, both ears of all mice were challenged on both sides by topical application of 20 µl 1% OXA dissolved in peanut oil. Ear thickness was measured prior to and at 24 hours or 48 hours after challenge using an Oditest spring calliper. Challenges and measurements were performed under light pentobarbital anaesthesia.

The intensity of the DTH reactions was measured according to the method described by van Loveren H., et al. (1984) J. Immunol. Methods 67: 311 and expressed according to the formula: $T_{t24/t48}-T_{t0}$ µm units, where t0, t24 and t48 represent the ear thickness at time 0, +24 hrs or +48 hrs after challenge respectively, in individual tests (T). The results are expressed as the mean +/- S.E.M.. The level of significance between means of the groups is obtained by Student's two-tailed t-test. The immunomodulating effect of the peptide is reflected in a significant difference in the increase or decrease in ear thickness as compared to the control (phosphate buffer).

Table 1 shows the structure of peptides 1–41 tested in the DTH test. The peptides show a significant difference in immunostimulatory and immunoinhibitory effect compared to control in at least one of the dosages tested.

TABLE 1

Peptides 1 to 41 give rise to an immunomodulatory response in the DTH Test.

1 Gly-Pro-Cys-Cys-Pro-Gly (SEQ ID NO:20)

2 Gly-Pro-Cys-Cys-Pro-Gly (SEQ ID NO:20) [Cys-Cys bridge]

3 Pro-Gly-Cys-Cys-Gly-Pro (SEQ ID NO:24)

4 Pro-Gly-Cys-Cys-Gly-Pro (SEQ ID NO:24) [Cys-Cys bridge]

5 Trp-Pro-Cys-Cys-Pro-Trp (SEQ ID NO:25) [Cys-Cys bridge]

6 Leu-Leu-Phe-Gly-Pro-Cys-Cys-NH2 (SEQ ID NO:41) [Cys-Cys bridge]

7 Ala-Pro-Cys-Cys-Val-Pro (SEQ ID NO:21)

8 Val-Ile-Cys-Cys-Leu-Thr (SEQ ID NO:26) [Cys-Cys bridge]

9 Thr-Pro-Cys-Cys-Phe-Ala (SEQ ID NO:27) [Cys-Cys bridge]

10 Glu-Glu-Cys-Cys-Phe-Tyr (SEQ ID NO:28) [Cys-Cys bridge]

11 Pro-Val-Cys-Cys-Ile-Gly (SEQ ID NO:42)

12 Pro-Val-Cys-Cys-Ile-Gly (SEQ ID NO:42) [Cys-Cys bridge]

13 Val-Cys-Ile-Cys-Gln (SEQ ID NO:50)

14 Leu-Ala-Cys-Cys-Val-Val (SEQ ID NO:45)

15 Val-Cys-Gly-Cys-Arg (SEQ ID NO:40)

16 Ser-Gln-Cys-Cys-Ser-Leu (SEQ ID NO:43) [Cys-Cys bridge]

17 Lys-Pro-Cys-Cys-Glu-Arg (SEQ ID NO:22)

18 Lys-Cys-Arg-Cys-Lys (SEQ ID NO:39) [Cys-Cys bridge]

19 Lys-Glu-Cys-Cys-Tyr-Val (SEQ ID NO:30)

20 Ser-Ile-Cys-Cys-Thr-Lys (SEQ ID NO:44) [Cys-Cys bridge]

21 Lys-Leu-Cys-Cys-Asp-Ile (SEQ ID NO:29) [Cys-Cys bridge]

22 Pro-Asp-Cys-Cys-Ile-Pro (SEQ ID NO:23)

23 Lys-Glu-Cys-Cys-Tyr-Val (SEQ ID NO:30) [Cys-Cys bridge]

24 Asp-Cys-Ile-Cys-Gln (SEQ ID NO:54)

25 Ile-Cys-Thr-Cys-Glu (SEQ ID NO:52) [Cys-Cys bridge]

26 Ile-Cys-Thr-Cys-Glu (SEQ ID NO:52)

27 Leu-Cys-Ala-Cys-Val (SEQ ID NO:53) [Cys-Cys bridge]

28 Lys-Leu-Cys-Cys-Gln-Met (SEQ ID NO:32)

29 Phe-Cys-Ile-Cys-Lys (SEQ ID NO:36)

30 Asp-Cys-Ile-Cys-Gln (SEQ ID NO:54) [Cys-Cys bridge]

31 Lys-Leu-Cys-Cys-Gln-Met (SEQ ID NO:32) [Cys-Cys bridge]

32 Ac-Ala-Pro-Cys-Cys-Val-Pro (SEQ ID NO:21)

33 Arg-Cys-Ser-Gly-Cys-Cys-Asn (SEQ ID NO:36)

34 Ala-Cys-Lys-Cys-Gln (SEQ ID NO:55)

35 Gly-Pro-Cys-Ile-Cys-Pro-Gly (SEQ ID NO:51)
   Gly-Pro-Cys-Ile-Cys-Pro-Gly (SEQ ID NO:51) [parallel Cys-Cys bridges]

36 Pro-Gly-Cys-Cys-Gly-Pro (SEQ ID NO:24)
   Pro-Gly-Cys-Cys-Gly-Pro (SEQ ID NO:24) [parallel Cys-Cys bridges]

37 Val-Cys-Gly-Cys-Arg (SEQ ID NO:40)
   Val-Cys-Gly-Cys-Arg (SEQ ID NO:40) [crossed Cys-Cys bridges]

38 Val-Cys-Gly-Cys-Arg (SEQ ID NO:40)
   Val-Cys-Gly-Cys-Arg (SEQ ID NO:40) [parallel Cys-Cys bridges]

39 Pro-Gly-Cys-Cys-Pro-Gly (SEQ ID NO:46) [Cys-Cys bridge]

TABLE 1-continued

Peptides 1 to 41 give rise to an immunomodulatory response in the DTH Test.

40  Ala-Pro-Cys-Cys-Glu-Ser (SEQ ID NO:49)
(Cys-Cys bridged)

41  Pro-Ala-Cys-Cys-Gly-Pro (SEQ ID NO:49)
(Cys-Cys bridged)

EXAMPLE 44

Comparison of the Immunomodulatory Effect of Peptide via Different Routes of Administration Peptide (Peptide No. 4-derived from SEQ ID NO:24) was administered to mice (groups of 10) orally and by parenteral injection (intravenous and subcutaneous injection) at doses of from 0.0003 µmol/kg body weight through to 3.0 µmol/kg body weight as per example 43. The animals were examined as per Example 43; changes in ear thickness noted. The mean and standard error of the mean for each group of mice (10 per group) was recorded. It was found that the administration of peptide by way of oral administration gives rise to a more marked immunomodulatory response than that observed when peptide is administered by other parenteral means.

EXAMPLE 45

Comparison of Immunomodulatory Effect on Administration of Peptide Dimer (Peptide Shown in Box 36 (SEQ ID NO:24) via Different Routes of Administration Peptide (SEQ ID NO:24, dimerized as shown in Box 36 of Table 1) was administered to mice (groups of 10) at doses of 0.03 µmol/kg body weight and 3.0 µmol/kg body weight. The animals were examined as per Example 43; changes in ear thickness noted. The mean and standard error of the mean for each group of mice (10 per group) was calculated. It was found that the peptide dimer produces a significant immunomodulatory effect in the DTH test relative to the control and that the oral route of administration gives rise to a stronger reaction relative to reactions observed on administration of peptides of the same dosage given by parenteral routes.

EXAMPLE 46

Effects of Peptides on Tumour Growth $10^4$ rat spontaneously developed mammary carcinoma cells in isotonic saline and 5% normal syngeneic rat serum were inoculated subcutaneously in the right hindlegs of Wistar rats (8 per group). Tumour size was estimated by palpation and caliper measurements of a first diameter (a), being the largest diameter, and the one (b) perpendicular to the first. The volume of the tumour was calculated using the formula: $V=0.4\ ab^2$.

Tumour volume is given in $mm^3$ as a median for each group of rats (8 per group).

Drug and control (isotonic saline) were administered by gavage (oesophageal tube) once a day (a.m.) on each of days 4–8 and 11–15 for peptides i) Gly-Pro-Cys-Cys-Pro-Gly (SEQ ID NO:20; 3 µmol/kg/day); ii) Ala-Pro-Cys-Cys-Val-Pro (SEQ ID NO:21; 0.03 and mol/kg/day);

iii)

Val-Ile-Cys-Cys-Leu-Thr (SEQ ID NO:26; 0.03 and 0.3 µmol/kg/day);
(Cys-Cys bridged)

and iv)

Pro-Gly-Cys-Cys-Gly-Pro (SEQ ID NO:20; 0.03 and 0.3 µmol/kg/day);
(Cys-Cys bridged)

and on each of days 6–9 and 13–20 for the peptide

Gly—Pro—Cys—Cys—Pro—Gly (SEQ ID NO:20; 0.003, 0.03, 0.3, and 3.0 µmol/kg/day).
(Cys-Cys bridged)

Results for SEQ ID NO:20 and SEQ ID NO:26 show a marked decrease in tumour volume compared with the control at all dose levels tested.

---

What is claimed is:

1. A peptide dimer comprising a first and a second peptide monomer, each monomer conforming to Formula (I):

$$(A)_n-X-Cys-Cys-Y-(B)_m \quad (I)$$

wherein
   each A is independently selected from the group consisting of an H, a protecting group, and a glycine, proline, or cysteine amino acid residue, wherein an amino acid residue at position "A" is in either an L- or a D-form;
   n is the integer one or the integer two;
   X is NH or a glycine or proline amino acid residue;
   Y is NH or a glycine or proline amino acid residue;
   each B is independently selected from the group consisting of an H, an OH, an $NH_2$, a protecting group, and a glycine, proline, or cysteine amino acid residue; and
   m is the integer one or the integer two;
   with the provisos that when A is not at least one amino acid residue, n is 1; when B is not at least one amino acid residue, m is 1; each peptide monomer contains no more than 6 amino acid residues; and the peptide dimer stimulates or inhibits an immune response in a mammal.

2. The peptide dimer of claim 1, wherein, in each monomer:

X is Gly and Y is Gly;
   X is Pro and Y is Pro; or
   X is Gly and Y is Pro.

3. The peptide dimer:

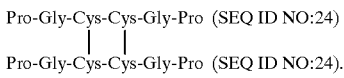

Pro-Gly-Cys-Cys-Gly-Pro (SEQ ID NO:24)
|  |
Pro-Gly-Cys-Cys-Gly-Pro (SEQ ID NO:24).

4. A peptide of Formula (I):

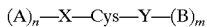

$$(A)_n\text{—}X\text{—}Cys\text{—}Y\text{—}(B)_m \quad (I)$$

wherein
  each A is independently selected from the group consisting of an H, a protecting group, and a glycine, proline, or cysteine amino acid residue, wherein an amino acid residue at position "A" is in either an L- or a D-form;
  n is the integer one or the integer two;
  X is selected from the group consisting of an NH and a glycine or proline amino acid residue;
  Y is NH or a glycine or proline amino acid residue;
  each B is independently selected from the group consisting of an H, an OH, an $NH_2$, a protecting group, and a glycine, proline or cysteine amino acid residue; and
  m is the integer one or the integer two;
  with the provisos that when A is not at least one amino acid residue, n is 1; when B is not at least one amino acid residue, m is 1; the peptide sequence contains no more than 6 amino acid residues; the peptide, or a dimer of the peptide stimulates or inhibits an immune response in a mammal; and, optionally, the peptide is combined with a transport agent.

5. The peptide of claim 4, wherein:
  X is Gly and Y is Gly;
  X is Pro and Y is Pro; or
  X is Gly and Y is Pro.

6. The peptide of claim 4, wherein the peptide is free from an added transport agent.

7. The peptide of claim 4, wherein the peptide is in the form of an acid addition salt.

8. The peptide of claim 7, wherein the acid addition salt is selected from the group consisting of hydrochloric, hydrobromic, nitric, perchloric, sulphuric, citric, tartaric, phosphoric, lactic, benzoic, glutamic, oxalic, aspartic, pyruvic, acetic, succinic, fumaric, maleic, oxaloacetic, isethionic, stearic, phthalic, methanesulphonic, p-toluene sulphonic, benzenesulphonic, lactobionic, and glucuronic acids.

9. The peptide of claim 4, wherein the peptide is in the form of a base salt.

10. The peptide of claim 9, wherein the base salt is selected from the group consisting of alkali metal salts, alkaline earth salts, organic base salts, and amino acid salts.

11. A pharmaceutical composition comprising the peptide of claim 4 and a pharmaceutically acceptable carrier therefor.

12. The pharmaceutical composition of claim 11, wherein the peptide is formulated for oral administration to a mammal.

13. The pharmaceutical composition of claim 12, wherein the amount of the peptide needed in the formulation to induce an observable level of stimulated or inhibited immune response in a mammal when administered orally is less than the amount of the peptide needed to achieve a similar level of immune response stimulation or inhibition in the mammal when administered parenterally.

14. The pharmaceutical composition of claim 12, wherein the peptide is free from an added transport agent.

15. The pharmaceutical composition of claim 12, wherein the peptide is in the form of an acid addition salt or a base salt.

16. The pharmaceutical composition of claim 11, wherein the peptide is formulated for intra-tracheal administration to a mammal.

17. The pharmaceutical composition of claim 16, wherein the amount of the peptide needed in the formulation to induce an observable level of stimulated or inhibited immune response in a mammal when administered intra-tracheally is less than the amount of the peptide needed to achieve a similar level of immune response stimulation or inhibition in the mammal when administered parenterally.

18. The pharmaceutical composition of claim 16, wherein the peptide is free from an added transport agent.

19. The pharmaceutical composition of claim 16, wherein the peptide is in the form of an acid addition salt or a base salt.

20. The pharmaceutical composition of claim 11, wherein the peptide is formulated for nasal administration to a mammal.

21. The pharmaceutical composition of claim 20, wherein the amount of the peptide needed in the formulation to induce an observable level of stimulated or inhibited immune response in a mammal when administered nasally is less than the amount of the peptide needed to achieve a similar level of immune response stimulation or inhibition in the mammal when administered parenterally.

22. The pharmaceutical composition of claim 20, wherein the peptide is free from an added transport agent.

23. The pharmaceutical composition of claim 20, wherein the peptide is in the form of an acid addition salt or a base salt.

24. A method for preparing a pharmaceutical composition comprising combining a peptide of claim 4, or a salt thereof, with a pharmaceutically acceptable carrier.

25. A method of making the peptide of claim 4 comprising a chemical process in which amino acid residues are joined to one another by a peptide bond, employing a protecting group before the bond is formed, after the bond is formed, or both before and after the bond is formed.

26. A method of stimulating or inhibiting an immune response in a mammal, the method comprising administering the peptide of claim 4 to the epithelial cell lining of the mammal in an amount sufficient to stimulate or inhibit an immune response in the mammal and thereby induce a therapeutic effect.

27. The method of claim 26, wherein the epithelial cell lining comprises mucosal associated lymphoid tissue.

28. The method of claim 26, wherein the peptide is free from an added transport agent.

29. A method of stimulating or inhibiting an immune response in a mammal, the method comprising administering a pharmaceutical composition comprising the peptide of claim 4 and a pharmaceutically acceptable carrier therefor to the epithelial cell lining of the mammal in an amount sufficient to stimulate or inhibit an immune response in the mammal and thereby induce a therapeutic effect.

30. The method of claim 29, wherein the pharmaceutical composition is formulated for oral administration.

31. The method of claim 29, wherein the pharmaceutical composition is formulated for intra-tracheal administration.

32. The method of claim 29, wherein the pharmaceutical composition is formulated for nasal administration.

33. A method of treating cancer, the method comprising administering to a mammal diagnosed as having cancer a therapeutically effective amount of a peptide of claim 4, or a salt thereof, wherein the peptide is an immunostimulatory peptide.

34. The method of claim 33, wherein the peptide is free from an added transport agent.

35. A method of treating cancer, the method comprising administering to a mammal diagnosed as having cancer a pharmaceutical composition comprising (a) the peptide of claim 4, or a salt thereof, and (b) a pharmaceutically acceptable carrier therefor, wherein the peptide is an immunostimulatory peptide.

36. The method of claim 35, wherein the pharmaceutical composition is formulated for oral administration.

37. The method of claim 35, wherein the pharmaceutical composition is formulated for intra-tracheal administration.

38. The method of claim 35, wherein the pharmaceutical composition is formulated for nasal administration.

39. A method of treating an autoimmune disease, the method comprising administering to a mammal diagnosed as having an autoimmune disease a pharmaceutical composition comprising (a) the peptide of claim 4, or a salt thereof, and (b) a pharmaceutically acceptable carrier therefor, wherein the peptide is an immunoinhibitory peptide.

40. The method of claim 39, wherein the pharmaceutical composition is formulated for oral administration.

41. The method of claim 39, wherein the pharmaceutical composition is formulated for intra-tracheal administration.

42. The method of claim 39, wherein the pharmaceutical composition is formulated for nasal administration.

43. A method of treating an autoimmune disease, the method comprising administering to a mammal diagnosed as having an autoimmune disease a therapeutically effective amount of a peptide of claim 4, or a salt thereof, wherein the peptide is an immunoinhibitory peptide.

44. The method of claim 43, wherein the peptide is free from an added transport agent.

45. The method of claim 43, wherein the autoimmune disease is rheumatoid arthritis.

46. A method of inhibiting transplant rejection in a mammal, the method comprising administering to the mammal a therapeutically effective amount of a peptide of claim 4, or a salt thereof, wherein the peptide is an immunoinhibitory peptide.

47. The method of claim 46, wherein the peptide is free from an added transport agent.

48. A method of inhibiting transplant rejection in a mammal, the method comprising administering to the mammal a pharmaceutical composition comprising (a) the peptide of claim 4, or a salt thereof, and (b) a pharmaceutically acceptable carrier therefor, wherein the peptide is an immunoinhibitory peptide.

49. The method of claim 48, wherein the pharmaceutical composition is formulated for oral administration.

50. The method of claim 48, wherein the pharmaceutical composition is formulated for intra-tracheal administration.

51. The method of claim 48, wherein the pharmaceutical composition is formulated for nasal administration.

52. A peptide of Formula (I):

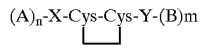

$$(A)_n\text{-}X\text{-}Cys\text{-}Cys\text{-}Y\text{-}(B)_m \quad (I)$$

wherein
each A is independently selected from the group consisting of an H, a protecting group, and a glycine, proline, or cysteine amino acid residue, wherein an amino acid residue at position "A" is in either an L- or a D-form;
n is the integer one or the integer two;
X is a glycine or proline amino acid residue;
Y is NH or a glycine or proline amino acid residue;
each B is independently selected from the group consisting of an H, an OH, an NH$_2$, a protecting group, and a glycine, proline or cysteine amino acid residue; and
m is the integer one or the integer two;
with the provisos that when A is not at least one amino acid residue, n is 1; when B is not at least one amino acid residue, m is 1; the peptide sequence contains no more than 6 amino acid residues; the peptide stimulates or inhibits an immune response in a mammal; and, optionally, the peptide is combined with a transport agent.

53. The peptide of claim 52, selected from the group consisting of:

Gly-Pro-Cys-Cys-Pro-Gly (SEQ ID NO:20) and

Pro-Gly-Cys-Cys-Gly-Pro (SEQ ID NO:24).

54. The peptide of claim 52, wherein the peptide is free from an added transport agent.

55. The peptide of claim 52, wherein the peptide is in the form of an acid addition salt.

56. The peptide of claim 55, wherein the acid addition salt is selected from the group consisting of hydrochloric, hydrobromic, nitric, perchloric, sulphuric, citric, tartaric, phosphoric, lactic, benzoic, glutamic, oxalic, aspartic, pyruvic, acetic, succinic, fumaric, maleic, oxaloacetic, isethionic, stearic, phthalic, methanesulphonic, p-toluene sulphonic, benzenesulphonic, lactobionic, and glucuronic acids.

57. The peptide of claim 52, wherein the peptide is in the form of a base salt.

58. The peptide of claim 52, wherein the base salt is selected from the group consisting of alkali metal salts, alkaline earth salts, organic base salts, and amino acid salts.

59. A pharmaceutical composition comprising the peptide of claim 52 and a pharmaceutically acceptable carrier therefor.

60. The pharmaceutical composition of claim 59, wherein the peptide is formulated for oral administration to a mammal.

61. The pharmaceutical composition of claim 60, wherein the amount of the peptide needed in the formulation to induce an observable level of stimulated or inhibited immune response in a mammal when administered orally is less than the amount of the peptide needed to achieve a similar level of immune response stimulation or inhibition in the mammal when administered parenterally.

62. The pharmaceutical composition of claim 60, wherein the peptide is free from an added transport agent.

63. The pharmaceutical composition of claim 60, wherein the peptide is in the form of an acid addition salt or a base salt.

64. The pharmaceutical composition of claim 59, wherein the peptide is formulated for intra-tracheal administration to a mammal.

65. The pharmaceutical composition of claim 64, wherein the amount of the peptide needed in the formulation to induce an observable level of stimulated or inhibited immune response in a mammal when administered intratracheally is less than the amount of the peptide needed to achieve a similar level of immune response stimulation or inhibition in the mammal when administered parenterally.

66. The pharmaceutical composition of claim 64, wherein the peptide is free from an added transport agent.

67. The pharmaceutical composition of claim 64, wherein the peptide is in the form of an acid addition salt or a base salt.

68. The pharmaceutical composition of claim 59, wherein the peptide is formulated for nasal administration to a mammal.

69. The pharmaceutical composition of claim 68, wherein the amount of the peptide needed in the formulation to induce an observable level of stimulated or inhibited immune response in a mammal when administered nasally is less than the amount of the peptide needed to achieve a similar level of immune response stimulation or inhibition in the mammal when administered parenterally.

70. The pharmaceutical composition of claim 68, wherein the peptide is free from an added transport agent.

71. The pharmaceutical composition of claim 68, wherein the peptide is in the form of an acid addition salt or a base salt.

72. A method for preparing a pharmaceutical composition comprising combining a peptide of claim 52, or a salt thereof, with a pharmaceutically acceptable carrier.

73. A method of making the peptide of claim 52 comprising a chemical process in which amino acid residues are joined to one another by a peptide bond, employing a protecting group before the bond is formed, after the bond is formed, or both before and after the bond is formed.

74. A method of stimulating or inhibiting an immune response in a mammal, the method comprising administering the peptide of claim 52 to the epithelial cell lining of the mammal in an amount sufficient to stimulate or inhibit an immune response in the mammal and thereby induce a therapeutic effect.

75. The method of claim 74, wherein the epithelial cell lining comprises mucosal associated lymphoid tissue.

76. The method of claim 74, wherein the peptide is administered free from an added transport agent.

77. A method of stimulating or inhibiting an immune response in a mammal, the method comprising administering a pharmaceutical composition comprising the peptide of claim 52 and a pharmaceutically acceptable carrier therefor to the epithelial cell lining of the mammal in an amount sufficient to stimulate or inhibit an immune response in the mammal and thereby induce a therapeutic effect.

78. The method of claim 77, wherein the pharmaceutical composition is formulated for oral administration.

79. The method of claim 77, wherein the pharmaceutical composition is formulated for intra-tracheal administration.

80. The method of claim 77, wherein the pharmaceutical composition is formulated for nasal administration.

81. A method of treating cancer, the method comprising administering to a mammal diagnosed as having cancer a therapeutically effective amount of a peptide of claim 52, or a salt thereof, wherein the peptide is an immunostimulatory peptide.

82. The method of claim 81, wherein the peptide is free from an added transport agent.

83. A method of treating cancer, the method comprising administering to a mammal diagnosed as having cancer a pharmaceutical composition comprising (a) the peptide of claim 52, or a salt thereof, and (b) a pharmaceutically acceptable carrier therefor, wherein the peptide is an immunostimulatory peptide.

84. The method of claim 83, wherein the pharmaceutical composition is formulated for oral administration.

85. The method of claim 83, wherein the pharmaceutical composition is formulated for intra-tracheal administration.

86. The method of claim 83, wherein the pharmaceutical composition is formulated for nasal administration.

87. A method of inhibiting transplant rejection in a mammal, the method comprising administering to the mammal a therapeutically effective amount of a peptide of claim 52, or a salt thereof, wherein the peptide is an immunoinhibitory peptide.

88. The method of claim 87, wherein the peptide is free from an added transport agent.

89. A method of inhibiting transplant rejection in a mammal, the method comprising administering to the mammal a pharmaceutical composition comprising (a) the peptide of claim 57, or a salt thereof, and (b) a pharmaceutically acceptable carrier therefor, wherein the peptide is an immunoinhibitory peptide.

90. The method of claim 89, wherein the pharmaceutical composition is formulated for oral administration.

91. The method of claim 89, wherein the pharmaceutical composition is formulated for intra-tracheal administration.

92. The method of claim 89, wherein the pharmaceutical composition is formulated for nasal administration.

* * * * *